US009283082B2

(12) United States Patent
Sanford et al.

(10) Patent No.: US 9,283,082 B2
(45) Date of Patent: Mar. 15, 2016

(54) METHODS RELATED TO SEATING OF BEARING COMPONENT ON TIBIAL TRAY

(71) Applicant: Zimmer, Inc., Warsaw, IN (US)

(72) Inventors: Adam H. Sanford, Los Angeles, CA (US); Brian D. Byrd, North Webster, IN (US); Ramesh Annayappa, Bangalore (IN); Jeffery A. VanDiepenbos, Syracuse, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/284,144

(22) Filed: May 21, 2014

(65) Prior Publication Data
US 2014/0257506 A1   Sep. 11, 2014

Related U.S. Application Data

(63) Continuation of application No. 13/189,324, filed on Jul. 22, 2011, now Pat. No. 8,764,840.

(60) Provisional application No. 61/367,374, filed on Jul. 24, 2010, provisional application No. 61/367,375, filed on Jul. 24, 2010.

(51) Int. Cl.
*A61F 2/38*       (2006.01)
*A61F 2/30*       (2006.01)

(52) U.S. Cl.
CPC ....... *A61F 2/389* (2013.01); *A61F 2002/30383* (2013.01); *A61F 2002/30387* (2013.01); *A61F 2002/30395* (2013.01); *A61F 2002/30401* (2013.01); *A61F 2002/30476* (2013.01);

(Continued)

(58) Field of Classification Search
CPC ....... A61F 2/38; A61F 2/3868; A61F 2/3886; A61F 2/389; A61F 2002/3895
See application file for complete search history.

(56) References Cited

U.S. PATENT DOCUMENTS

| 4,016,606 A | 4/1977 | Murray et al. |
| 4,340,978 A | 7/1982 | Buechel et al. |

(Continued)

FOREIGN PATENT DOCUMENTS

| AU | 2011286306 B2 | 10/2014 |
| CA | 2190029 A1 | 11/1995 |

(Continued)

OTHER PUBLICATIONS

"U.S. Appl. No. 13/189,324, PTO Response to Rule 312 Communication mailed May 29, 2014", 2 pgs.

(Continued)

*Primary Examiner* — Marcia Watkins
(74) *Attorney, Agent, or Firm* — Schwegman Lundberg & Woessner, P.A.

(57) ABSTRACT

A tibial prosthesis has a bearing component configured for an anterior-medial insertion, which advantageously avoids the extensor mechanism of the knee. A tibial tray may include a banana-shaped boss that corresponds to a notch formed in the bearing component. After the bearing component is inserted along the anterior-medial path, the boss is received within the notch by rotating the bearing component with respect to the tibial tray. This rotation seats the bearing component upon the tibial tray in the manner of a fixed-bearing prosthesis. Alternatively, the boss and notch may define angled central axes which allow straight anterior-medial insertion of the bearing component and locking engagement to the tibial tray.

15 Claims, 13 Drawing Sheets

(52) U.S. Cl.
CPC .......... *A61F 2002/30576* (2013.01); *A61F 2002/30616* (2013.01); *A61F 2002/30883* (2013.01)

(56) References Cited

U.S. PATENT DOCUMENTS

| | | | |
|---|---|---|---|
| 4,714,474 A | 12/1987 | Brooks, Jr. et al. |
| 4,769,040 A | 9/1988 | Wevers |
| 4,770,661 A | 9/1988 | Oh |
| 4,795,468 A | 1/1989 | Hodorek et al. |
| 4,822,365 A | 4/1989 | Walker et al. |
| 4,936,853 A | 6/1990 | Fabian et al. |
| 4,950,298 A | 8/1990 | Gustilo et al. |
| 4,959,071 A | 9/1990 | Brown et al. |
| 4,963,152 A | 10/1990 | Hofmann et al. |
| 5,047,058 A | 9/1991 | Roberts et al. |
| 5,061,271 A | 10/1991 | Van Zile |
| 5,071,438 A | 12/1991 | Jones et al. |
| 5,133,758 A | 7/1992 | Hollister |
| 5,137,536 A | 8/1992 | Koshino |
| 5,192,328 A | 3/1993 | Winters |
| 5,219,362 A | 6/1993 | Tuke et al. |
| 5,236,461 A | 8/1993 | Forte |
| 5,246,459 A | 9/1993 | Elias |
| 5,271,737 A | 12/1993 | Baldwin et al. |
| 5,282,861 A | 2/1994 | Kaplan |
| 5,282,868 A | 2/1994 | Bahler |
| 5,282,870 A | 2/1994 | Moser et al. |
| 5,290,313 A | 3/1994 | Heldreth |
| 5,310,480 A | 5/1994 | Vidueira |
| 5,326,361 A | 7/1994 | Hollister |
| 5,344,460 A | 9/1994 | Turanyi et al. |
| 5,370,699 A | 12/1994 | Hood et al. |
| 5,405,396 A | 4/1995 | Heldreth et al. |
| 5,413,604 A | 5/1995 | Hodge |
| 5,413,605 A | 5/1995 | Ashby et al. |
| 5,507,820 A | 4/1996 | Pappas |
| 5,549,688 A | 8/1996 | Ries et al. |
| 5,556,433 A | 9/1996 | Gabriel et al. |
| 5,609,639 A | 3/1997 | Walker |
| 5,609,641 A | 3/1997 | Johnson et al. |
| 5,609,645 A | 3/1997 | Vinciuerra |
| 5,613,970 A | 3/1997 | Houston et al. |
| 5,658,344 A | 8/1997 | Hurlburt |
| 5,702,463 A | 12/1997 | Pothier et al. |
| 5,755,802 A | 5/1998 | Gerber |
| 5,824,100 A | 10/1998 | Kester et al. |
| 5,824,102 A | 10/1998 | Buscayret |
| 5,871,539 A | 2/1999 | Pappas |
| 5,879,394 A | 3/1999 | Ashby et al. |
| 5,928,286 A | 7/1999 | Ashby et al. |
| 5,964,808 A | 10/1999 | Blaha et al. |
| 6,004,351 A | 12/1999 | Tomita et al. |
| 6,010,534 A | 1/2000 | O'neil et al. |
| 6,013,103 A | 1/2000 | Kaufman et al. |
| 6,039,764 A | 3/2000 | Pottenger et al. |
| 6,068,658 A | 5/2000 | Insall et al. |
| 6,074,425 A | 6/2000 | Pappas |
| 6,090,144 A | 7/2000 | Letot et al. |
| 6,102,954 A | 8/2000 | Albrektsson et al. |
| 6,102,955 A | 8/2000 | Mendes et al. |
| 6,197,064 B1 | 3/2001 | Haines et al. |
| 6,203,576 B1 | 3/2001 | Afriat et al. |
| 6,206,927 B1 | 3/2001 | Fell et al. |
| RE37,277 E | 7/2001 | Baldwin et al. |
| 6,258,127 B1 | 7/2001 | Schmotzer |
| 6,306,172 B1 | 10/2001 | O'neil et al. |
| 6,379,388 B1 | 4/2002 | Ensign et al. |
| 6,413,279 B1 | 7/2002 | Metzger et al. |
| 6,491,726 B2 | 12/2002 | Pappas |
| 6,506,215 B1 | 1/2003 | Letot et al. |
| 6,506,216 B1 | 1/2003 | McCue et al. |
| 6,709,461 B2 | 3/2004 | O'Neil et al. |
| 6,755,864 B1 | 6/2004 | Brack et al. |
| 6,770,078 B2 | 8/2004 | Bonutti |
| 6,869,448 B2 | 3/2005 | Tuke et al. |
| 6,923,832 B1 | 8/2005 | Sharkey et al. |
| 6,953,479 B2 | 10/2005 | Carson et al. |
| 6,986,791 B1 | 1/2006 | Metzger |
| 7,025,788 B2 | 4/2006 | Metzger et al. |
| 7,083,652 B2 | 8/2006 | McCue et al. |
| 7,153,326 B1 | 12/2006 | Metzger |
| 7,189,262 B2 | 3/2007 | Hayes, Jr. et al. |
| 7,264,635 B2 | 9/2007 | Suguro et al. |
| 7,294,149 B2 | 11/2007 | Hozack et al. |
| 7,309,362 B2 | 12/2007 | Yasuda et al. |
| 7,445,639 B2 | 11/2008 | Metzger et al. |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,585,328 B2 | 9/2009 | Haas |
| 7,625,407 B2 | 12/2009 | Akizuki et al. |
| 7,628,818 B2 | 12/2009 | Hazebrouck et al. |
| 7,635,390 B1 | 12/2009 | Bonutti |
| 7,695,519 B2 | 4/2010 | Collazo |
| 7,850,698 B2 | 12/2010 | Straszheim-Morley et al. |
| 8,568,486 B2 | 10/2013 | Wentorf et al. |
| 8,574,304 B2 | 11/2013 | Wentorf et al. |
| 8,591,594 B2 | 11/2013 | Parisi et al. |
| 8,613,775 B2 | 12/2013 | Wentorf et al. |
| 8,628,580 B2 | 1/2014 | Sanford et al. |
| 8,758,444 B2 | 6/2014 | Wentorf et al. |
| 8,764,840 B2 | 7/2014 | Sanford et al. |
| 2001/0047210 A1 | 11/2001 | Wolf |
| 2002/0072802 A1 | 6/2002 | O'Neil et al. |
| 2002/0120340 A1 | 8/2002 | Metzger et al. |
| 2002/0161448 A1 | 10/2002 | Hayes, Jr. et al. |
| 2004/0034432 A1 | 2/2004 | Hughes et al. |
| 2004/0153066 A1 | 8/2004 | Coon et al. |
| 2004/0162620 A1 | 8/2004 | Wyss |
| 2004/0186582 A1 | 9/2004 | Yasuda et al. |
| 2004/0204765 A1* | 10/2004 | Fenning et al. ............ 623/20.29 |
| 2004/0267371 A1 | 12/2004 | Hayes, Jr. et al. |
| 2005/0096747 A1 | 5/2005 | Tuttle et al. |
| 2005/0143831 A1 | 6/2005 | Justin et al. |
| 2005/0143832 A1 | 6/2005 | Carson |
| 2005/0209702 A1 | 9/2005 | Todd et al. |
| 2005/0246030 A1* | 11/2005 | Yao ......................... 623/20.33 |
| 2005/0267584 A1 | 12/2005 | Burdulis, Jr. et al. |
| 2006/0030945 A1 | 2/2006 | Wright |
| 2006/0142869 A1 | 6/2006 | Gross |
| 2006/0161259 A1 | 7/2006 | Cheng et al. |
| 2006/0195195 A1 | 8/2006 | Burstein et al. |
| 2006/0224244 A1 | 10/2006 | Thomas et al. |
| 2007/0010890 A1 | 1/2007 | Collazo |
| 2007/0129808 A1* | 6/2007 | Justin et al. ............... 623/20.15 |
| 2007/0135926 A1 | 6/2007 | Walker |
| 2007/0198022 A1 | 8/2007 | Lang et al. |
| 2007/0233269 A1 | 10/2007 | Steines et al. |
| 2008/0021566 A1 | 1/2008 | Peters et al. |
| 2008/0051908 A1 | 2/2008 | Angibaud et al. |
| 2008/0091271 A1 | 4/2008 | Bonitati et al. |
| 2008/0091272 A1 | 4/2008 | Aram et al. |
| 2008/0091273 A1 | 4/2008 | Hazebrouck |
| 2008/0114462 A1 | 5/2008 | Guidera et al. |
| 2008/0167722 A1 | 7/2008 | Metzger et al. |
| 2008/0215156 A1 | 9/2008 | Duggal et al. |
| 2008/0243258 A1 | 10/2008 | Sancheti |
| 2008/0281426 A1 | 11/2008 | Fitz et al. |
| 2008/0288080 A1 | 11/2008 | Sancheti |
| 2009/0036992 A1 | 2/2009 | Tsakonas |
| 2009/0082873 A1 | 3/2009 | Hazebrouck et al. |
| 2009/0088862 A1 | 4/2009 | Thomas et al. |
| 2009/0125114 A1 | 5/2009 | May et al. |
| 2009/0149963 A1 | 6/2009 | Sekel |
| 2009/0149964 A1 | 6/2009 | May et al. |
| 2009/0204222 A1 | 8/2009 | Burstein et al. |
| 2009/0222103 A1 | 9/2009 | Fitz et al. |
| 2009/0306786 A1 | 12/2009 | Samuelson |
| 2009/0319047 A1 | 12/2009 | Walker |
| 2010/0016978 A1 | 1/2010 | Williams et al. |
| 2010/0016979 A1 | 1/2010 | Wyss et al. |
| 2010/0063594 A1 | 3/2010 | Hazebrouck et al. |
| 2010/0100189 A1 | 4/2010 | Metzger |

(56) References Cited

U.S. PATENT DOCUMENTS

| | | |
|---|---|---|
| 2010/0100191 A1 | 4/2010 | May et al. |
| 2010/0125339 A1 | 5/2010 | Earl et al. |
| 2010/0152858 A1 | 6/2010 | Lu et al. |
| 2010/0191341 A1 | 7/2010 | Byrd |
| 2010/0222890 A1 | 9/2010 | Barnett et al. |
| 2010/0305708 A1 | 12/2010 | Lang et al. |
| 2010/0329530 A1 | 12/2010 | Lang et al. |
| 2011/0082559 A1 | 4/2011 | Hartdegen et al. |
| 2011/0087332 A1 | 4/2011 | Bojarski et al. |
| 2011/0144760 A1 | 6/2011 | Wong et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford et al. |
| 2012/0101585 A1 | 4/2012 | Parisi et al. |
| 2013/0024001 A1 | 1/2013 | Wentorf et al. |
| 2013/0131820 A1 | 5/2013 | Wentorf et al. |
| 2014/0025175 A1 | 1/2014 | Wentorf et al. |
| 2014/0025176 A1 | 1/2014 | Wentorf et al. |
| 2014/0025177 A1 | 1/2014 | Wentorf et al. |
| 2014/0052268 A1 | 2/2014 | Sanford et al. |
| 2014/0156015 A1 | 6/2014 | Parisi et al. |
| 2014/0249641 A1 | 9/2014 | Wentorf et al. |

FOREIGN PATENT DOCUMENTS

| | | |
|---|---|---|
| CH | 687584 A5 | 1/1997 |
| CN | 2768715 Y | 4/2006 |
| CN | 1874738 A | 12/2006 |
| CN | 101347359 A | 1/2009 |
| CN | 101401750 A | 4/2009 |
| CN | 101683289 A | 3/2010 |
| CN | 103118634 A | 5/2013 |
| CN | 103118635 A | 5/2013 |
| CN | 103118636 A | 5/2013 |
| CN | 104093380 A | 10/2014 |
| CN | 104203160 A | 12/2014 |
| EP | 0021421 A1 | 1/1981 |
| EP | 0340919 A1 | 11/1989 |
| EP | 340919 A1 | 11/1989 |
| EP | 0372811 A1 | 6/1990 |
| EP | 0306744 B1 | 4/1992 |
| EP | 0495340 A1 | 7/1992 |
| EP | 0672397 A1 | 9/1995 |
| EP | 0552950 B1 | 9/1996 |
| EP | 0536457 B1 | 1/1997 |
| EP | 0642328 B1 | 12/1998 |
| EP | 0956836 A1 | 11/1999 |
| EP | 0956836 B1 | 11/1999 |
| EP | 1097679 A1 | 5/2001 |
| EP | 0709074 B1 | 12/2002 |
| EP | 1327424 A1 | 7/2003 |
| EP | 1396240 B1 | 4/2008 |
| EP | 1996122 A1 | 12/2008 |
| EP | 0927009 B1 | 1/2009 |
| EP | 1555962 B1 | 2/2011 |
| EP | 2319460 A1 | 5/2011 |
| EP | 2324799 A2 | 5/2011 |
| EP | 2335654 A1 | 6/2011 |
| EP | 2347733 A1 | 7/2011 |
| EP | 0689808 B1 | 9/2012 |
| EP | 2595573 A1 | 5/2013 |
| EP | 2782525 A1 | 10/2014 |
| FR | 2736819 A1 | 1/1997 |
| FR | 2747914 A1 | 10/1997 |
| FR | 2778332 A1 | 11/1999 |
| FR | 2788964 A1 | 8/2000 |
| FR | 2926719 A1 | 7/2009 |
| GB | 2253147 A | 9/1992 |
| GB | 2345446 A | 7/2000 |
| IN | 7145DELNP2014 A | 4/2015 |
| JP | 62270153 A | 11/1987 |
| JP | 09511668 A | 11/1997 |
| JP | 2000245758 A | 9/2000 |
| JP | 2003516183 A | 5/2003 |
| JP | 2004254811 A | 9/2004 |
| JP | 3734270 B2 | 1/2006 |
| JP | 2011092738 A | 5/2011 |
| JP | 2013535276 A | 9/2013 |
| JP | 2013536005 A | 9/2013 |
| JP | 2013536006 A | 9/2013 |
| JP | 2013536007 A | 9/2013 |
| JP | 2015504333 A | 2/2015 |
| JP | 2015504759 A | 2/2015 |
| WO | WO-9305729 A2 | 4/1993 |
| WO | WO-9409725 A1 | 5/1994 |
| WO | WO-9514444 A1 | 6/1995 |
| WO | WO-9530389 A1 | 11/1995 |
| WO | WO-9535074 A1 | 12/1995 |
| WO | WO-9934755 A1 | 7/1999 |
| WO | WO-0141680 A1 | 6/2001 |
| WO | WO-03099106 A2 | 12/2003 |
| WO | WO-2005037147 A1 | 4/2005 |
| WO | WO-2005051240 A1 | 6/2005 |
| WO | WO-2006058057 A2 | 6/2006 |
| WO | WO-2007108804 A1 | 9/2007 |
| WO | WO-2007109641 A2 | 9/2007 |
| WO | WO-2009029631 A1 | 3/2009 |
| WO | WO-2009088238 A2 | 7/2009 |
| WO | WO-2010008803 A2 | 1/2010 |
| WO | WO-2010045537 A1 | 4/2010 |
| WO | WO-2011072235 A2 | 6/2011 |
| WO | WO-2012018563 A1 | 2/2012 |
| WO | WO-2012018564 A1 | 2/2012 |
| WO | WO-2012018565 A1 | 2/2012 |
| WO | WO-2012018566 A1 | 2/2012 |
| WO | WO-2012018567 A1 | 2/2012 |
| WO | WO-2012112698 A2 | 8/2012 |
| WO | WO-2013077919 A1 | 5/2013 |
| WO | WO-2013115849 A1 | 8/2013 |

OTHER PUBLICATIONS

"Australian Application Serial No. 2011286307, Response filed May 21, 2014 to First Examiner Report mailed Oct. 17, 2013", 16 pgs.

"Australian Application Serial No. 2012341026, Statement of Proposed Amendment filed Jun. 18, 2014", 25 pgs.

"International Application Serial No. PCT/US2012/052132, International Preliminary Report on Patentability mailed Jun. 5, 2014", 12 pgs.

"U.S. Appl. No. 13/594,543, Final Office Action mailed Jul. 17, 2014", 12 pgs.

"U.S. Appl. No. 13/594,543, Response filed Dec. 17, 2014 to Final Office Action dated Jul. 17, 2014", 15 pgs.

"U.S. Appl. No. 14/034,937, Non Final Office Action mailed Jan. 2, 2015", 21 pgs.

"U.S. Appl. No. 14/034,937, Response filed Oct. 27, 2014 to Restriction Requirement mailed Sep. 11, 2014", 12 pgs.

"U.S. Appl. No. 14/034,937, Restriction Requirement mailed Sep. 11, 2014", 6 pgs.

"U.S. Appl. No. 14/034,944, Response filed Dec. 15, 2014 to Restriction Requirement mailed Oct. 14, 2014", 12 pgs.

"U.S. Appl. No. 14/034,944, Restriction Requirement mailed Oct. 14, 2014", 6 pgs.

"U.S. Appl. No. 14/034,954, Non Final Office Action mailed Dec. 19, 2014", 25 pgs.

"U.S. Appl. No. 14/034,954, Response filed Oct. 27, 2014 to Restriction Requirement mailed Aug. 25, 2014", 11 pgs.

"U.S. Appl. No. 14/034,954, Restriction Requirement mailed Aug. 25, 2014", 7 pgs.

"U.S. Appl. No. 14/034,963, Non Final Office Action mailed Nov. 21, 2014", 19 pgs.

"Australian Application Serial No. 2012341026, First Examiner Report mailed Jul. 14, 2014", 2 pgs.

"Australian Application Serial No. 2012341026, Response filed Nov. 21, 2014 to First Examiner Report mailed Jul. 14, 2014", 1 pg.

"Canadian Application Serial No. 2,856,571, Office Action mailed Jul. 22, 2014", 2 pgs.

(56) References Cited

OTHER PUBLICATIONS

"European Application Serial No. 11738918.9, Examination Notification Art. 94(3) mailed Oct. 23, 2014", 5 pgs.
"European Application Serial No. 11738919.7, Examination Notification Art. 94(3) mailed Jul. 7, 2014", 4 pgs.
"European Application Serial No. 11738919.7, Response filed Nov. 13, 2014 to Examination Notification Art. 94(3) mailed Jul. 7, 2014", 14 pgs.
"International Application Serial No. PCT/US2012/052340, International Preliminary Report on Patentability mailed Aug. 14, 2014", 8 pgs.
"Japanese Application Serial No. 2013-521854, Notice of Reason for Rejection mailed Sep. 16, 2014", (W/ English Translation), 6 pgs.
"Japanese Application Serial No. 2013-521855, Amendment filed Jul. 22, 2014", (W/ English Translation), 20 pgs.
"U.S. Appl. No. 13/189,324, Examiner Interview Summary mailed Jan. 13, 2014", 4 pgs.
"U.S. Appl. No. 13/189,324, Final Office Action mailed Jul. 16, 2013", 19 pgs.
"U.S. Appl. No. 13/189,324, Non Final Office Action mailed Dec. 11, 2012", 19 pgs.
"U.S. Appl. No. 13/189,324, Notice of Allowance mailed Feb. 20, 2014", 8 pgs.
"U.S. Appl. No. 13/189,324, Response filed Jan. 15, 2014 to Final Office Action dated Jul. 16, 2013", 23 pgs.
"U.S. Appl. No. 13/189,324, Response filed Jun. 10, 2013 to Non Final Office Action mailed Dec. 11, 2012", 24 pgs.
"U.S. Appl. No. 13/189,328, Non Final Office Action mailed Mar. 19, 2013", 10 pgs.
"U.S. Appl. No. 13/189,328, Notice of Allowance mailed Oct. 8, 2013", 12 pgs.
"U.S. Appl. No. 13/189,328, PTO Response to 312 Amendment mailed Dec. 13, 2013", 2 pgs.
"U.S. Appl. No. 13/189,328, Response filed Jan. 10, 2013 to Restriction Requirement mailed Dec. 10, 2012", 9 pgs.
"U.S. Appl. No. 13/189,328, Response filed Jul. 18, 2013 to Non Final Office Action mailed Mar. 19, 2013", 16 pgs.
"U.S. Appl. No. 13/189,328, Restriction Requirement mailed Dec. 10, 2012", 6 pgs.
"U.S. Appl. No. 13/189,336, Notice of Allowance mailed Sep. 13, 2013", 30 pgs.
"U.S. Appl. No. 13/189,336, PTO Response to 312 Amendment mailed Nov. 25, 2013", 2 pgs.
"U.S. Appl. No. 13/189,336, Response filed Apr. 15, 2013 to Restriction Requirement mailed Jan. 30, 2013", 21 pgs.
"U.S. Appl. No. 13/189,336, Response filed Jul. 17, 2013 to Restriction Requirement mailed Jul. 17, 2013", 20 pgs.
"U.S. Appl. No. 13/189,336, Restriction Requirement mailed Jan. 30, 2013", 5 pgs.
"U.S. Appl. No. 13/189,336, Restriction Requirement mailed Jun. 17, 2013", 6 pgs.
"U.S. Appl. No. 13/189,338, Notice of Allowance mailed Sep. 23, 2013", 23 pgs.
"U.S. Appl. No. 13/189,338, Response filed Apr. 15, 2013 to Restriction Requirement mailed Feb. 14, 2013", 18 pgs.
"U.S. Appl. No. 13/189,338, Response filed Jul. 17, 2013 to Restriction Requirement mailed Jun. 17, 2013", 16 pgs.
"U.S. Appl. No. 13/189,338, Restriction Requirement mailed Feb. 14, 2013", 5 pgs.
"U.S. Appl. No. 13/189,338, Restriction Requirement mailed Jun. 17, 2013", 6 pgs.
"U.S. Appl. No. 13/189,339, Notice of Allowance mailed Sep. 20, 2013", 16 pgs.
"U.S. Appl. No. 13/189,339, Response filed Apr. 15, 2013 to Restriction Requirement mailed Mar. 6, 2013", 11 pgs.
"U.S. Appl. No. 13/189,339, Response filed Jul. 17, 2013 to Restriction Requirement mailed Jun. 17, 2013", 10 pgs.
"U.S. Appl. No. 13/189,339, Restriction Requirement mailed Mar. 6, 2013", 6 pgs.
"U.S. Appl. No. 13/189,339, Restriction Requirement mailed Jun. 17, 2013", 7 pgs.
"U.S. Appl. No. 13/229,103, Examiner Interview Summary mailed Sep. 13, 2013", 3 pgs.
"U.S. Appl. No. 13/229,103, Non Final Office Action mailed Apr. 1, 2013", 18 pgs.
"U.S. Appl. No. 13/229,103, Notice of Allowance mailed Sep. 18, 2013", 9 pgs.
"U.S. Appl. No. 13/229,103, Response filed Jul. 1, 2013 to Non Final Office Action mailed Apr. 1, 2013", 19 pgs.
"U.S. Appl. No. 13/229,103, Supplemental Notice of Allowability mailed Oct. 18, 2013", 2 pgs.
"U.S. Appl. No. 13/593,339, Non Final Office Action mailed Oct. 4, 2013", 7 pgs.
"U.S. Appl. No. 13/593,339, Notice of Allowance mailed Feb. 14, 2014", 9 pgs.
"U.S. Appl. No. 13/593,339, Preliminary Amendment filed Aug. 23, 2012", 6 pgs.
"U.S. Appl. No. 13/593,339, Response filed Jan. 31, 2014 to Non-Final Office Action dated Oct. 4, 2013", 19 pgs.
"U.S. Appl. No. 13/593,339, Response filed Aug. 30, 2013 to Restriction Requirement mailed Aug. 1, 2013", 14 pgs.
"U.S. Appl. No. 13/593,339, Restriction Requirement mailed Aug. 1, 2013", 5 pgs.
"U.S. Appl. No. 13/593,339, Supplemental Notice of Allowability mailed Mar. 31, 2014", 2 pgs.
"U.S. Appl. No. 13/594,543, Non Final Office Action mailed Dec. 26, 2013", 15 pgs.
"U.S. Appl. No. 13/594,543, Preliminary Amendment filed Aug. 24, 2012", 4 pgs.
"U.S. Appl. No. 13/594,543, Response filed May 7, 2014 to Non-Final office Action dated Dec. 26, 2013", 17 pgs.
"U.S. Appl. No. 13/594,543, Response filed Oct. 11, 2013 to Restriction Requirement mailed Sep. 12, 2013", 8 pgs.
"U.S. Appl. No. 13/594,543, Restriction Requirement mailed Sep. 12, 2013", 5 pgs.
"U.S. Appl. No. 14/034,937, Preliminary Amendment filed Sep. 24, 2013", 3 pgs.
"U.S. Appl. No. 14/034,937, Supplemental Preliminary Amendment filed Oct. 24, 2013", 11 pgs.
"U.S. Appl. No. 14/034,944, Preliminary Amendment filed Sep. 24, 2013", 3 pgs.
"U.S. Appl. No. 14/034,944, Supplemental Preliminary Amendment filed Oct. 24, 2013", 11 pgs.
"U.S. Appl. No. 14/034,954, Preliminary Amendment filed Sep. 24, 2013", 3 pgs.
"U.S. Appl. No. 14/034,954, Supplemental Preliminary Amendment filed Oct. 25, 2013", 8 pgs.
"U.S. Appl. No. 14/034,963, Preliminary Amendment filed Sep. 24, 2013", 3 pgs.
"U.S. Appl. No. 14/063,593, Preliminary Amendment filed Oct. 25, 2013", 3 pgs.
"Australian Application Serial No. 2011286306, First Examiner Report mailed Jun. 19, 2013", 4 pgs.
"Australian Application Serial No. 2011286307, First Examiner Report mailed Oct. 17, 2013", 2 pgs.
"Australian Application Serial No. 2011286308, First Examiner Report mailed Jun. 21, 2013", 4 pgs.
"Australian Application Serial No. 2011286309, First Examiner Report mailed Jun. 21, 2013", 3 pgs.
"Bi-Cruciate Stabilized Knee System", Design Rationale, Smith & Nephew Journal, (2006), 20 pgs.
"European Application Serial No. 11815029.1, Extended European Search Report mailed Dec. 10, 2013", 8 pgs.
"Extramedullary/Intramedullary Tibial Resector: Surgical Technique", Nexgen Complete Knee Solution, Zimmer, Inc. 97-5997-02 Rev 1, (2000, 2002), 25 pgs.
"Extramedullary/Intramedullary Tibial Resector: Surgical Technique", Nexgen Complete Knee Solution, Zimmer, Inc., (2000, 2008, 2009), 28 pgs.
"Gender Solutions Natural-Knee Flex System", Zimmer, Inc., (2007, 2009), 6 pgs.

(56) References Cited

OTHER PUBLICATIONS

"International Application Serial No. PCT/US2011/045077, International Preliminary Report on Patentability mailed Jul. 5, 2012", 23 pgs.
"International Application Serial No. PCT/US2011/045077, International Search Report and Written Opinion mailed Jan. 9, 2012", 15 pgs.
"International Application Serial No. PCT/US2011/045078, International Preliminary Report on Patentability mailed Feb. 7, 2013", 11 pgs.
"International Application Serial No. PCT/US2011/045078, International Search Report and Written Opinion mailed Jan. 9, 2012", 14 pgs.
"International Application Serial No. PCT/US2011/045080, International Preliminary Report on Patentability mailed Feb. 7, 2013", 13 pgs.
"International Application Serial No. PCT/US2011/045080, International Search Report mailed Jan. 9, 2012", 7 pgs.
"International Application Serial No. PCT/US2011/045080, Written Opinion mailed Jan. 9, 2012", 11 pgs.
"International Application Serial No. PCT/US2011/045082, International Preliminary Report on Patentability mailed Feb. 7, 2013", 11 pgs.
"International Application Serial No. PCT/US2011/045082, International Search Report mailed Jan. 9, 2012", 5 pgs.
"International Application Serial No. PCT/US2011/045082, Written Opinion mailed Jan. 9, 2012", 10 pgs.
"International Application Serial No. PCT/US2011/045083, International Preliminary Report on Patentability mailed Feb. 7, 2013", 8 pgs.
"International Application Serial No. PCT/US2011/045083, International Search Report mailed Dec. 7, 2011", 2 pgs.
"International Application Serial No. PCT/US2011/045083, Written Opinion mailed Dec. 7, 2011", 6 pgs.
"International Application Serial No. PCT/US2011/051021, International Preliminary Report on Patentability mailed Mar. 21, 2013", 8 pgs.
"International Application Serial No. PCT/US2011/051021, International Search Report mailed Nov. 23, 2011", 12 pgs.
"International Application Serial No. PCT/US2011/051021, Written Opinion mailed Nov. 23, 2011", 7 pgs.
"International Application Serial No. PCT/US2012/052132, International Search Report mailed Jan. 10, 2013", 5 pgs.
"International Application Serial No. PCT/US2012/052132, Invitation to Pay Additional Fees and Partial Search Report mailed Nov. 15, 2012", 7 pgs.
"International Application Serial No. PCT/US2012/052132, Written Opinion mailed Jan. 10, 2013", 10 pgs.
"International Application Serial No. PCT/US2012/052340, Search Report mailed Oct. 12, 2012", 4 pgs.
"International Application Serial No. PCT/US2012/052340, Written Opinion mailed Oct. 12, 2012", 6 pgs.
"LPS-Flex Fixed Bearing Knee: Surgical Technique", Zimmer, Inc., (2004, 2007, 2008), 16 pgs.
"NexGen Trabecular Metal Modular Plates", Zimmer Inc., (2007), 19 pgs.
"South African Application Serial No. 2013/01327, Amendment filed Apr. 24, 2014", 4 pgs.
"South African Application Serial No. 2013/01328, Amendment filed Apr. 24, 2014", 4 pgs.
"Surgical Technique for the CR-Flex Fixed Bearing Knee", NexGen Complete Knee Solution, Zimmer, Inc., (2003), 22 pgs.
"Tibial Baseplate: Pocket Guide (United States Version)", Zimmer, Inc. (2009), 17 pgs.
"Trabecular Metal Monoblock Tibial Components", Zimmer, Inc., (2007), 4 pgs.
"Trabecular Metal Monoblock Tibial Components Surgical Technique Addendum", Nexgen Zimmer, Inc., (2005, 2007), 12 pgs.
"Trabecular Metal Tibial Tray: Surgical Technique", NexGen Zimmer, Inc., (2007, 2009), 16 pgs.
Annayappa, Ramesh, et al., "Tibial Prosthesis", U.S. Appl. No. 13/189,324, filed Jul. 22, 2011, 50 pgs.
Annayappa, Ramesh, "Tibial Prosthesis", U.S. Appl. No. 13/189,328, filed Jul. 22, 2011, 82 pgs.
Ding, M., et al., "Age-related variations in the microstructure of human tibial cancellous bone", Journal of Orthopaedic Research, 20(3), (2002), 615-621.
Ding, M., et al., "Changes in the three-dimensional microstructure of human tibial cancellous bone in early osteoarthritis", Journal of Bone & Joint Surgery (British), 85-B(6), (Aug. 2003), 906-912.
Doyle, et al., "Comparative Analysis of Human Trabecular Bone and Polyurethane Foam", Purdue University., 1 pg.
Dunbar, M. J., et al., "Fixation of a Trabecular Metal Knee Arthroplasty Component: A Prospective Randomized Study", The Journal of Bone & Joint Surgery (American), vol. 91A(7), (Jul. 2009), 1578-1586.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Hvid, Ivan, et al., "Trabecular bone Strength Patterns at the Proximal Tibial Epiphysis", Journal of Orthopaedic Research, vol. 3, No. 4, (1985), 464-472.
Klostermann, et al., "Distribution of bone mineral density with age and gender in the proximal tibia", Clinical Biomechanics 19, 376-376.
Lorenz, Stephan, et al., "Radiological evaluation of the anterolateral and posteromedial bundle insertion sites of the posterior cruciate ligament", Knee Surg Sports Traumatol Arthosc, vol. 17, (2009), 683-690.
Moorman, Claude, et al., "Tibial Insertion of the Posterior Cruciate Ligament: A Sagittal Plane Analysis Using Gross, Histologic, and Radiographic Methods", Arthroscopy: The Journal of Arthroscopic and Related Surgery, vol. 24, No. 3, (Mar. 2008), 269-275.
Parisi, Raymond C, "Motion Facilitating Tibial Components for a Knee Prosthesis", U.S. Appl. No. 13/229,103, filed Sep. 9, 2011, 46 pgs.
Stilling, et al., "Superior fixation of pegged trabecular metal over screw-fixed pegged porous titanium fiber mesh", Acta Orthopaedica., (2011), 177-186.
Wentorf, Mary S. S, "Asymmetric Tibial Components for a Knee Prosthesis", U.S. Appl. No. 13/189,339, filed Jul. 22, 2011, 52 pgs.
Wentorf, Mary S. S, "Asymmetric Tibial Components for a Knee Prosthesis", U.S. Appl. No. 13/189,338, filed Jul. 22, 2011, 58 pgs.
Wentorf, Mary S. S, "Asymmetric Tibial Components for a Knee Prosthesis", U.S. Appl. No. 13/189,336, filed Jul. 22, 2011, 60 pgs.
"U.S. Appl. No. 13/594,543, Non Final Office Action mailed Jun. 19, 2015", 30 pgs.
"U.S. Appl. No. 14/034,937, Final Office Action mailed Jun. 5, 2015", 22 pgs.
"U.S. Appl. No. 14/034,963, Response filed Sep. 19, 2015 to Final Office Action mailed Apr. 13, 2015", 17 pgs.
"Japanese Application Serial No. 2014-542301, Office Action mailed May 12, 2015", (W/ English Translation), 6 pgs.
"PFC Sigma Knee System with Rotating Platform Technical/ Monograph", Depuy PFC Sigma RP, 0611-29-050 (Rev. 3), (1999), 70 pgs.
"U.S. Appl. No. 13/229,103, Applicant Interview Summary mailed Sep. 23, 2013", 2 pgs.
"U.S. Appl. No. 13/594,543, Non-Final Office Action mailed Jan 9, 2015", 23 pgs.
"U.S. Appl. No. 13/594,543, Response filed Apr. 7, 2015 to Non-Final Office Action mailed Jan. 9, 2015", 27 pgs.
"U.S. Appl. No. 14/034,937, Response filed Mar. 3, 2015 to Non-Final Office Action", 24 pgs.
"U.S. Appl. No. 14/034,944, Non Final Office Action mailed Mar. 3, 2015", 16 pgs.
"U.S. Appl. No. 14/034,954, Final Office Action mailed Jun. 1, 2015", 26 pgs.
"U.S. Appl. No. 14/034,954, Response filed Mar. 17, 2015 to Non Final Office Action mailed Dec. 19, 2014", 21 pgs.
"U.S. Appl. No. 14/034,963, Final Office Action mailed Apr. 13, 2015", 22 pgs.

(56) References Cited

OTHER PUBLICATIONS

"U.S. Appl. No. 14/034,963, Response filed Mar. 20, 2015 to Non-Final Office Action mailed Nov. 21, 2014", 20 pgs.

"Australian Application Serial No. 2011286306, Response filed Jun. 3, 2014 First Examiner Report mailed Jun. 19, 2013", 16 pgs.

"Canadian Application Serial No. 2,856,571 Response filed Jan. 22, 2015 to Office Action mailed Jul. 22, 2014", 24 pgs.

"Chinese Application Serial No. 201180045673.3, Office Action mailed Mar. 29, 2015", (W/ English Translation), 6 pgs.

"Chinese Application Serial No. 201180045681.8, Office Action mailed Jan. 22, 2015", (W/ English Translation), 11 pgs.

"Chinese Application Serial No. 201180045681.8, Response filed May 14, 2015 to Office Action mailed Jan. 22, 2015", W/ English Claims, 17 pgs.

"Chinese Application Serial No. 201180045683.7, Office Action mailed Mar. 9, 2015", (W/ English Translation), 6 pgs.

"Chinese Application Serial No. 201180045689.4, Office Action mailed Jan. 5, 2015", (W/ English Translation), 4 pgs.

"Chinese Application Serial No. 201180045689.4, Response filed May 1, 2015 to Office Action mailed Jan. 5, 2015", W/ English Claims, 13 pgs.

"Chinese Application Serial No. 201280071940.9, Preliminary Amendment filed Mar. 23, 2015", W/ English Claims, 11 pgs.

"European Application Serial No. 11738918.9, Preliminary Amendment mailed Sep. 24, 2013", 11 pgs.

"European Application Serial No. 11738918.9, Response filed Mar. 2, 2015 to Examination Notification Art. 94(3) mailed Oct. 23, 2014", 14 pgs.

"European Application Serial No. 11738919.7, Preliminary Amendment filed Nov. 4, 2013", 25 pgs.

"European Application Serial No. 11738920.5, Preliminary Amendment Sep. 24, 2013", 9 pgs.

"European Application Serial No. 11758060.5, Preliminary Amendment filed Nov. 4, 2013", 15 pgs.

"European Application Serial No. 11815029.1, Response filed Jul. 21, 2014 Extended European Search Report mailed Dec. 10, 2013", 15 pgs.

"European Application Serial No. 12756058.9, Preliminary Amendment filed Apr. 20, 2015", 12 pgs.

"European Application Serial No. 12756869.9 Response filed Feb. 10, 2015 to Communication Pursuant to Rule 161(1) and 162 EPC mailed Jul. 31, 2014", 14 pgs.

"Japanese Application Serial No. 2013-521854, Response filed Dec. 16, 2014 to Notice of Reason for Rejection mailed Sep. 16, 2014", W/ English Claims, 11 pgs.

"Japanese Application Serial No. 2013-521855, Office Action mailed May 24, 2015", W/ English Translation, 8 pgs.

"Mexican Application Serial No. MX/A/2013/000990, Office Action mailed Feb. 19, 2015", (W/ English Translation), 4 pgs.

"Mexican Application Serial No. MX/A/2013/000990, Response filed Apr. 29, 2015 to Office Action mailed Feb. 19, 2015", W/ English Claims, 18 pgs.

"Russian Application Serial No. 2013106942, Office Action mailed Apr. 16, 2015", W/ English Translation, 5 pgs.

\* cited by examiner

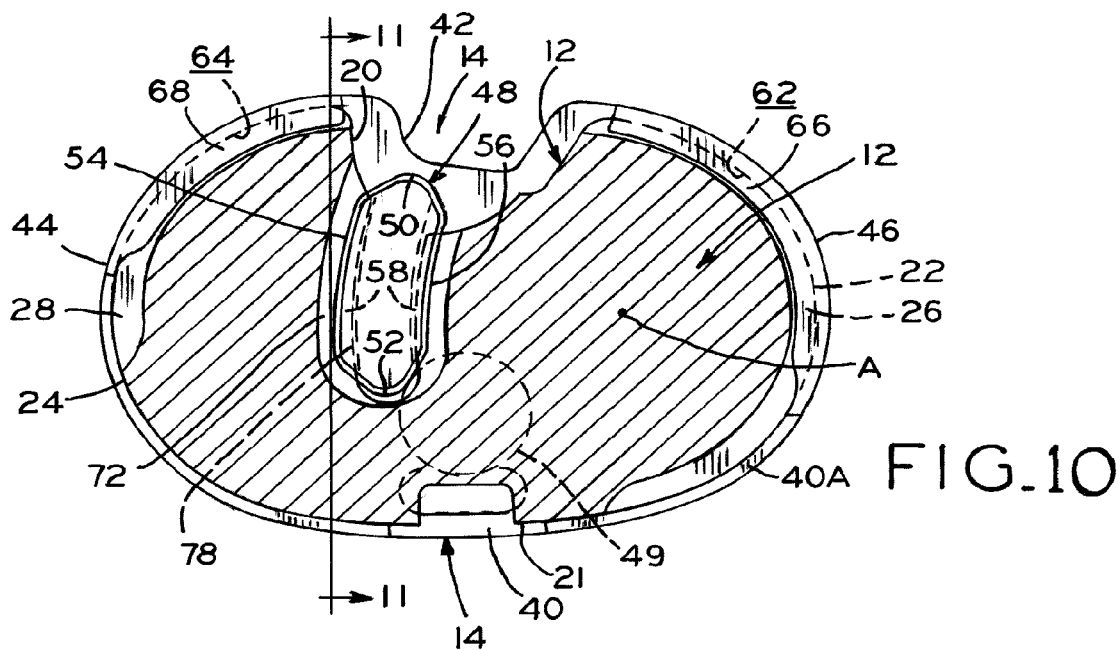
FIG_10
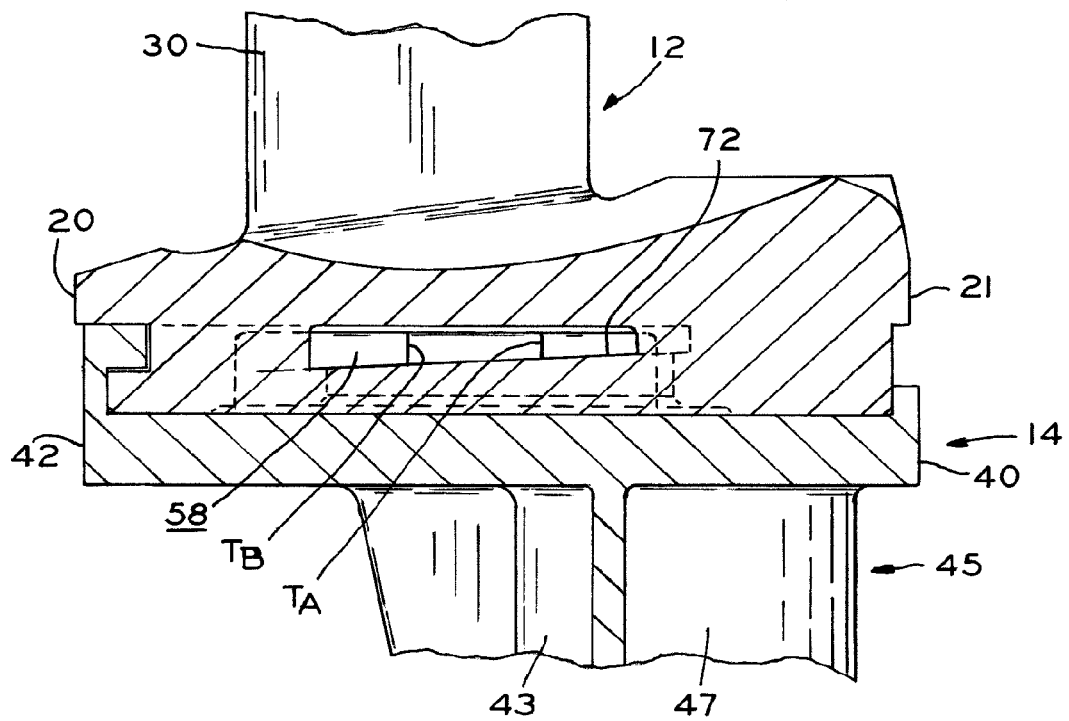
FIG_11

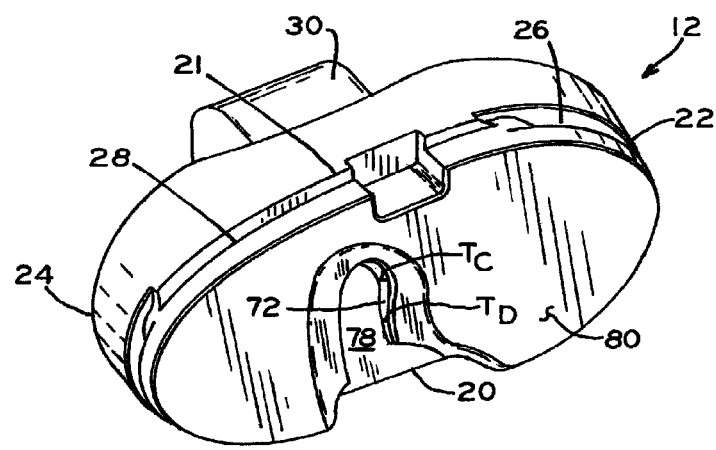
FIG_12

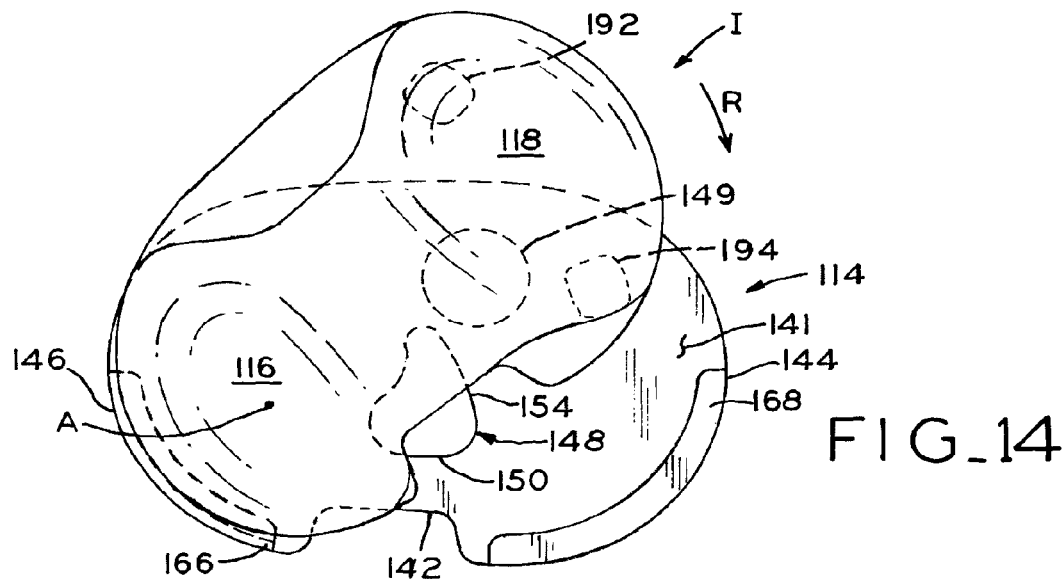
FIG_14
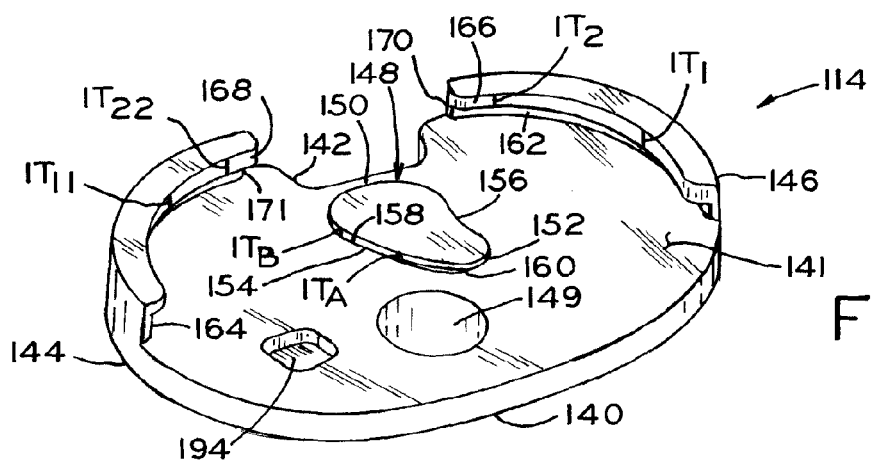
FIG_15
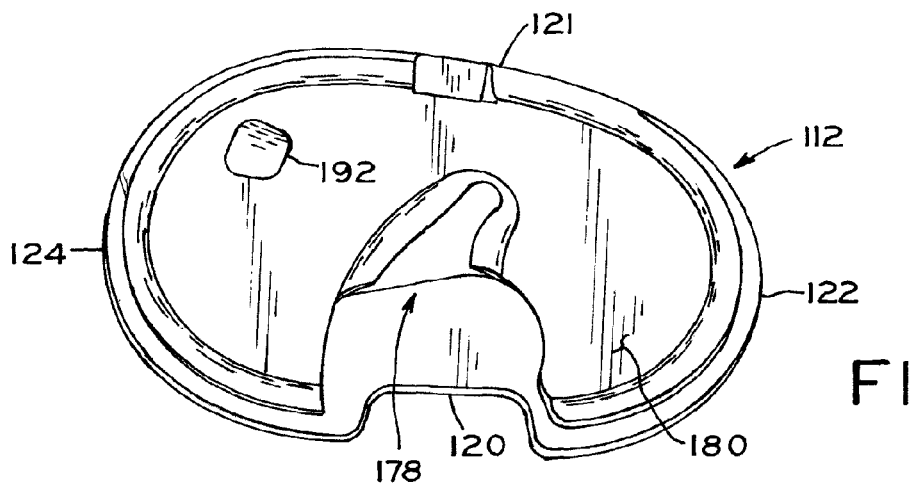
FIG_16

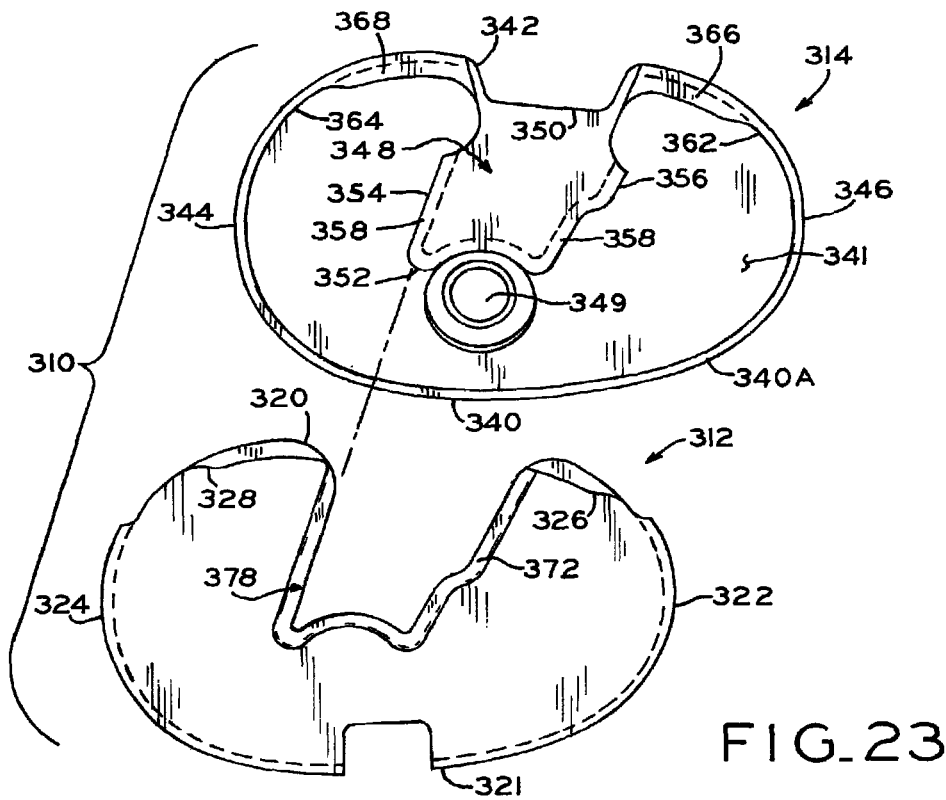
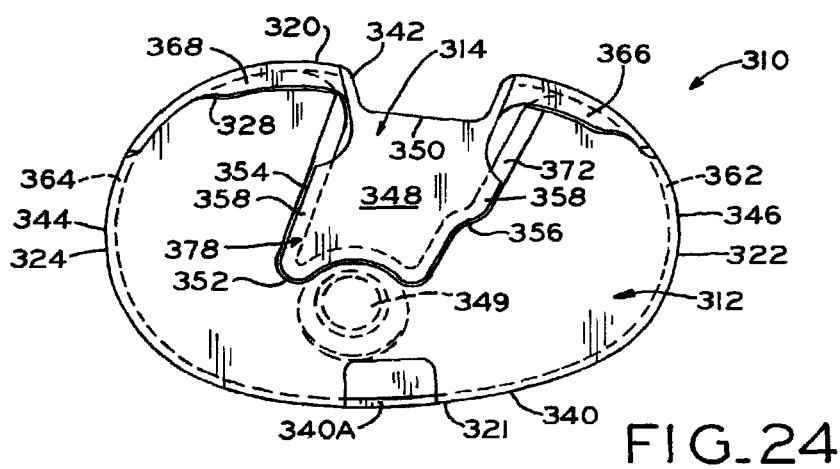

METHODS RELATED TO SEATING OF BEARING COMPONENT ON TIBIAL TRAY

CROSS-REFERENCE TO RELATED APPLICATIONS

This application is a continuation of U.S. patent application Ser. No. 13/189,324, filed on Jul. 22, 2011 and entitled TIBIAL PROSTHESIS now U.S. Pat. No. 8,764,840, which claims the benefit under Title 35, U.S.C. §119(e) of U.S. Provisional Patent Application Ser. No. 61/367,374, filed on Jul. 24, 2010 and entitled TIBIAL PROSTHESIS, and U.S. Provisional Patent Application Ser. No. 61/367,375, filed on Jul. 24, 2010 and entitled TIBIAL PROSTHESIS, the entire disclosures of which are hereby expressly incorporated by reference herein.

BACKGROUND

1. Field of the Invention

The present invention relates to orthopedic prostheses and, particularly, to proximal tibial prostheses.

2. Description of the Related Art

Orthopedic prostheses are commonly utilized to repair and/or replace damaged bone and tissue in the human body. For example, a knee prosthesis may be implanted during a total knee arthroplasty to replace damaged or destroyed bone in the tibia and/or femur and to recreate the natural, anatomical articulation of the knee joint. The knee prosthesis may include a femoral prosthesis shaped to replicate one or both of the natural femoral condyles. After resecting the distal end of the femur, one side of the femoral prosthesis is secured to the femur and the opposing side of the femoral prosthesis is configured for articulation against a tibial prosthesis.

A tibial prosthesis may include a first bearing component having a concave articular portion configured for articulation with the femoral prosthesis. The bearing component of the tibial prosthesis may be secured to a tibial tray. The tibial tray has a side secured to the bone stock of a resected proximal tibia. By securing the bearing component of the tibial prosthesis to the tibial tray to prevent translation and/or rotation of the bearing component relative to the tibial tray, a fixed bearing tibial prosthesis is created. The bearing component of the tibial prosthesis may be made from a polymeric material to facilitate articulation with the femoral component, while the tibial tray of the tibial prosthesis may be made from a metallic material to provide sufficient strength and rigidity to the tibial prosthesis. The femoral prosthesis and the tibial prosthesis seek to replicate the natural, anatomical articulation of the knee joint.

SUMMARY

The present disclosure provides a tibial prosthesis with a bearing component configured for an anterior-medial insertion, which advantageously avoids the extensor mechanism of the knee. A tibial tray may include a banana-shaped boss that corresponds to a notch formed in the bearing component. After the bearing component is inserted along the anterior-medial path, the boss is received within the notch by rotating the bearing component with respect to the tibial tray. This rotation seats the bearing component upon the tibial tray in the manner of a fixed-bearing prosthesis. Alternatively, the boss and notch may define angled central axes which allow straight anterior-medial insertion of the bearing component and locking engagement to the tibial tray.

For the purposes of this document, "anterior-medial insertion" means insertion along a path from a starting point displaced anteriorly and medially from the desired implanted position.

After the initial anterior-medial insertion, the bearing component may be rotated to a position that provides for proper final alignment of the bearing component with the tibial tray. A locking mechanism is used during this rotation to fix the bearing component to the tibial tray. Alternatively, the bearing component may be inserted along an anterior-medial insertion path and urged into a fixed position with the tibial tray along a single anterior-medial insertion trajectory. A locking mechanism engages as the bearing component is urged into the fixed position to lock the bearing component to the tibial tray when the bearing component is at the end of its travel. The locking mechanism fixes the bearing component to the tibial tray, which prevents relative movement therebetween such that the tibial prosthesis is a "fixed-bearing" design. Advantageously, the anterior-medial insertion avoids the extensor mechanism of the knee during the implantation of the bearing component.

The tibial tray may have a boss that is banana-shaped from a proximal-distal plan view and that corresponds to and is received into a notch of the bearing component. The boss has a pair of elongated sides, one concave and one convex. The concave side faces the lateral edge of the tibial tray, and the convex side faces the medial edge of the tibial tray. The geometry of the tibial boss allows an anterior-medially inserted bearing component to be rotated about a laterally positioned axis of rotation to complete seating of the bearing component atop the tibial tray.

The tibial tray may alternatively have a boss with a pair of angled, elongated sides, one of which faces a lateral edge and the other of which faces a medial edge of the tibial tray. The elongated sides may each angled about 8 to 10 degrees from an axis that is positioned through an anterior edge of the tibial tray and that is parallel to a sagittal plane of a body, though angles ranging from between about 0 to 90 degrees are contemplated. The geometry of this alternative tibial boss allows an anterior-medially inserted bearing component to be urged into a final, fixed position along an anterior-medial insertion trajectory corresponding to the angle of the elongated sides of the tibial tray boss to complete seating of the bearing component atop the tibial tray.

As used herein, "micromotion" refers to the small motions that may exist between prosthesis components, such as between tibial tray 14 and bearing component 12, upon application of force. Such small motions may occur as a result of material deformation in one or both of the interacting components, or may result from slight spaces or clearances therebetween, for example. Micromotion is distinguished from "mobile bearing" applications, which experience relatively larger motions as a tibial bearing articulates with respect to a tibial tray (such as by sliding or rotating) along a desired motion path.

As used herein, a "fixed bearing" tibial prosthesis is a prosthesis in which a bearing component is seated atop the tibial tray in a final, locked position. In this locked position, lift-off of the bearing component from the tibial tray as well as transverse movement of the bearing component relative to the tibial tray is prevented during natural articulation of the knee. While some micromotion may exist between the tibial bearing component and tibial tray in a fixed bearing prosthesis, no such motion occurs by design along a designated path.

A locking mechanism may be employed to fix the bearing component to the tibial tray, thereby creating a fixed bearing prosthesis. Such as a mechanism may including a dovetail boss on the tibial tray cooperating with a corresponding notch on a bearing component, a peripheral rail of the tibial tray cooperating with a corresponding recessed portion of the bearing component, a pair of anterior wedges projecting from an anterior edge of the bearing component that cooperate with an undercut within an anterior peripheral rail of the tibial tray, or any combination of these devices. Locking mechanisms of the present disclosure may also dictate the insertion trajectory of the bearing component relative to the tibial tray.

In one form thereof, the present disclosure provides a tibial prosthesis for replacing at least part of a natural knee, the tibial prosthesis comprising: a bearing component comprising: a proximal surface defining at least one concave articulating surface, and a distal surface opposite the proximal surface, the distal surface having a notch formed therein; and a tibial tray comprising: a support surface sized to support the distal surface of the bearing component, the support surface having a lateral edge and a medial edge, and a boss projecting proximally from the support surface, the boss having a concave lateral side facing the lateral edge of the tibial tray and a convex medial side facing the medial edge of the tibial tray, the bearing component rotatable about an axis of rotation between a disassembled position and an assembled position, the axis of rotation displaced laterally from the medial side of the boss, such that rotation of the bearing component from the disassembled position to the assembled position advances the boss of the tibial tray into the notch of the bearing component, the bearing component locked to the tibial tray in the assembled position to create a fixed bearing prosthesis.

In another form thereof, the present disclosure provides a method of inserting a bearing component onto a tibial tray via an incision providing access to a knee, the knee having an extensor mechanism, the method comprising: providing a tibial tray having a support surface sized to receive the bearing component; positioning the tibial tray within the knee via the incision; providing the bearing component having at least one concave articulating surface and an opposing distal surface; inserting the bearing component, while avoiding the extensor mechanism, through the incision in an anterior-medial insertion direction to position a distal surface of the bearing component atop the support surface of the tibial tray; and seating the bearing component onto the tibial tray.

In another form thereof, the present disclosure provides a tibial prosthesis for replacing at least part of a natural knee, the tibial prosthesis comprising: a bearing component comprising: at least one concave articulating surface; a distal surface opposite the concave articulating surface; and a distal tab projecting distally from the distal surface, the distal tab having a distal tab perimeter; and a tibial tray comprising: a support surface sized to support the distal surface of the bearing component, the support surface having a lateral edge and a medial edge; a proximal depression formed in the support surface and sized to receive of the distal tab of the bearing component, the proximal depression having a proximal depression perimeter, the proximal depression perimeter substantially congruent to the distal tab perimeter; and a ramped proximal groove sized to receive the distal tab of the bearing component, the ramped proximal groove having an anterior end at an anterior edge of the tibial tray and a posterior end adjacent the proximal depression.

BRIEF DESCRIPTION OF THE DRAWINGS

The above-mentioned and other features and advantages of this disclosure, and the manner of attaining them, will become more apparent and the invention itself will be better understood by reference to the following descriptions of embodiments of the invention taken in conjunction with the accompanying drawings, wherein:

FIG. 10 is a proximal, partial sectional plan view of the tibial prosthesis after rotation of the bearing component into a final, locked position atop the tibial tray of the first embodiment;

FIG. 11 is a cross-sectional view of the tibial prosthesis of FIG. 10 taken along line 11-11' of FIG. 10;

FIG. 12 is an anterior perspective view of the bearing component of the first embodiment;

FIG. 14 is a proximal plan view of the tibial prosthesis of the second embodiment including the tibial tray and a bearing component;

FIG. 15 is an anterior perspective view of the tibial tray of the second embodiment;

FIG. 16 is a distal plan view of the bearing component of the second embodiment;

FIG. 23 is a proximal plan view of the tibial prosthesis showing an anterior-medial insertion at an angle of the bearing component onto the tibial tray of the fourth embodiment;

FIG. 24 is a proximal plan view of the tibial prosthesis of the fourth embodiment, with the bearing component fully seated on the tibial tray.

Corresponding reference characters indicate corresponding parts throughout the several views. The exemplifications set out herein illustrate exemplary embodiments of the invention, and such exemplifications are not to be construed as limiting the scope of the disclosure in any manner.

DETAILED DESCRIPTION

To implant a tibial prosthesis including a tibial tray and a bearing component, the proximal portion of a patent's tibia is resected to provide a substantially flat surface for receipt of the tibial tray. Once the proximal tibia is resected, the tibial tray may be positioned on the proximal tibial in a location and orientation that maximizes coverage of the resected tibial surface while avoiding or minimizing overhang beyond the resected surface. With the tibial baseplate secured, the bearing component may be inserted onto the tibial tray via an incision made to access a knee during surgery. Minimally invasive surgical techniques and associated implant components may be used.

The knee prosthesis and associated methods of the present disclosure desirably allow for implantation of a bearing component for securement atop an implanted tibial tray along an anterior-medial insertion path which, advantageously, allows for implantation of the bearing component without disturbing the extensor mechanism of the knee.

Figure 25:
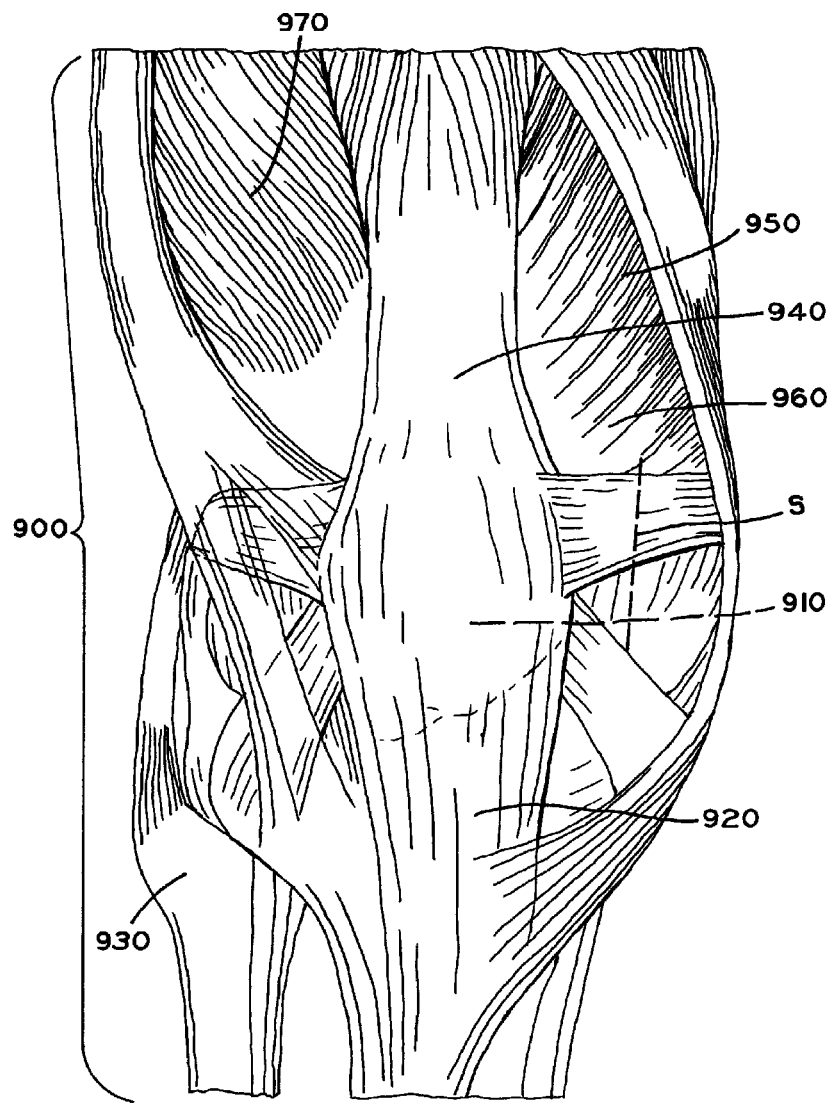
FIG. 25 is an anatomical view of a right knee showing the extensor mechanism of the knee and an exemplary incision made to access the knee.

FIG. 25 shows an anatomical view of the extensor mechanism of the knee, which is a complex interaction of knee muscles, ligaments, and tendons that stabilize the patellofemoral joint made up of the patella 910 and distal end of the femur (not shown). Fibula 930 is located at a lateral side of the tibia (not shown). Included among the extensor mechanism muscles are the front thigh muscles of the knee, or quadriceps, that insert into patella 910 and act to extend the knee and control side-to-side movement of patella 910. The quadriceps include the rectus femoris (not shown), quadriceps tendon 940, and vastus medialis 950. Vastus medialis 950 includes vastus medialis obliquus 960 and vastus lateralis 970. FIG. 25 further shows an example of incision S made to access the knee, though other types and positions of incisions are contemplated within the scope of this disclosure for the purpose of accessing the knee and implanting a tibial prosthesis.

The methods of this disclosure utilize a tibial knee prosthesis that is implantable into the knee in a manner that avoids the extensor mechanism described above. The exemplary embodiments of the present disclosure described below include a tibial tray that is provided by a medical professional, such as a surgeon, and positioned within the knee through incision S. The tibial tray includes a bearing component support, which is sized and shaped to receive a bearing component. The bearing component is also provided by the medical professional (e.g., surgeon) and is also inserted through incision S. The first three exemplary embodiments each have bearing components that are inserted in an anterior-medial insertion direction through incision S and are then rotated to a final seating position atop the tibial tray. An exemplary fourth embodiment includes a bearing component that is inserted in an anterior-medial insertion direction and which can be moved to a final, seated position by movement along the anterior-medial insertion trajectory alone, with no final rotational movement.

Figure 1:
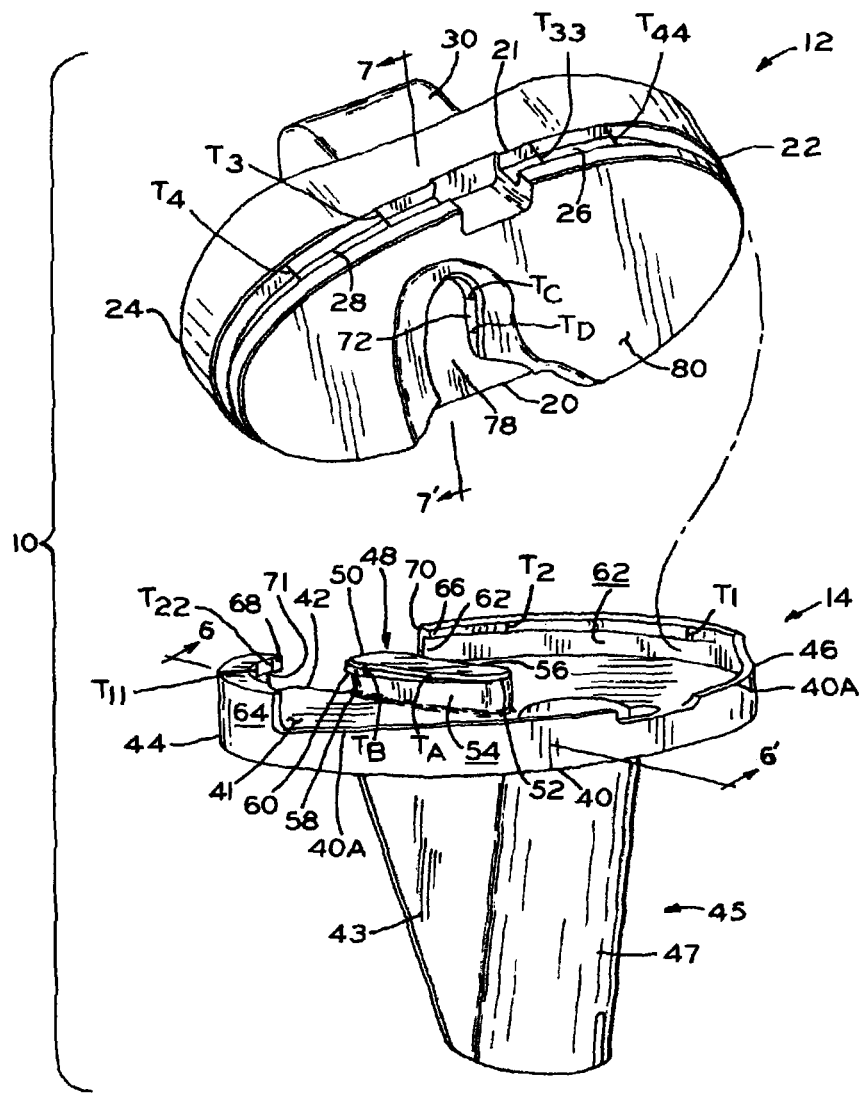
FIG. 1 is an exploded anterior perspective view of a tibial prosthesis made in accordance with a first embodiment of the present invention, including a bearing component and a tibial tray.
Figure 2:
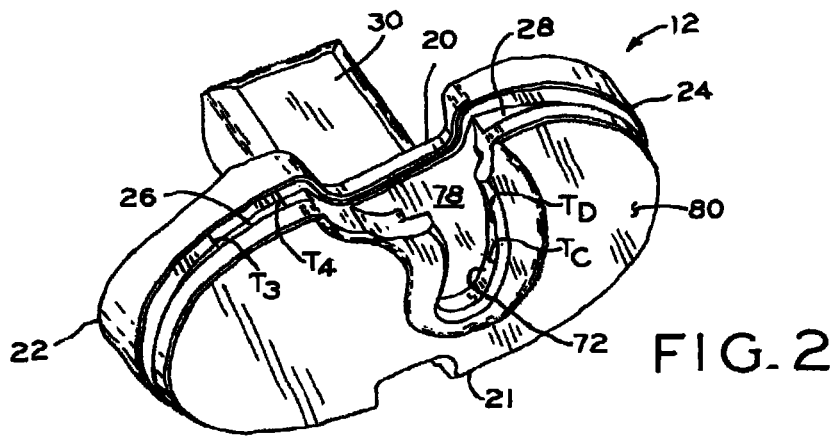
FIG. 2 is a posterior perspective view of the bearing component of the first embodiment.

The first exemplary embodiment, described below in detail, allows for a rotational seating of a bearing component atop a tibial tray. Referring to FIG. 1, tibial prosthesis 10 is shown in a disassembled condition and includes bearing component 12, which is securable to tibial tray 14. While shown and described herein with specific reference to a left knee application, tibial prosthesis 10 may also be configured for use in a right knee application. Right and left knee configurations are mirror images of one another about a sagittal plane, and it is contemplated that all aspects of the prostheses described herein are equally applicable to a left- or right-knee configuration. Moreover, it will be appreciated that the principles of the present disclosure are also applicable to other mammalian joints, such as the human hip, shoulder, elbow, ankle, and the like.

Figure 3:
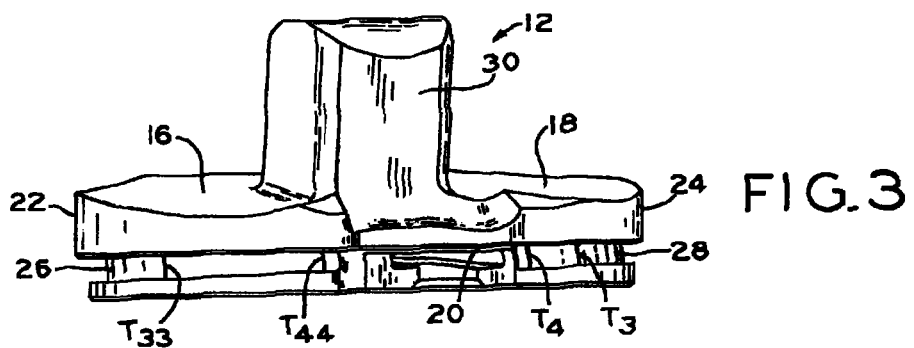
FIG. 3 is a posterior-lateral elevation view of the bearing component of the first embodiment.
Figure 4:
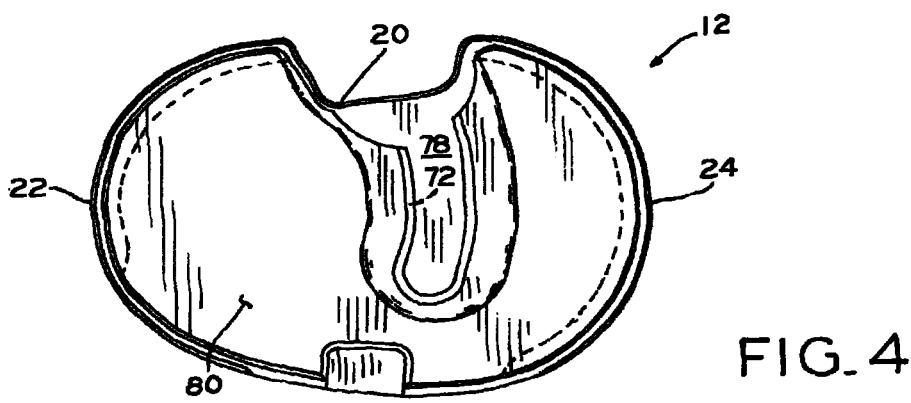
FIG. 4 is a distal plan view of the bearing component of the first embodiment.

Referring to FIG. 3, bearing component 12 includes a pair of opposing articulating surfaces 16 and 18 that are configured for articulation against opposing condyles of a femur or femoral prosthesis (not shown). Extending upwardly between opposing articulating surfaces 16 and 18 is tibial eminence or spine 30. While bearing component 12 is shown and described herein as including tibial spine 30, it is envisioned that tibial spine 30 may also be absent as required or desired for a particular surgery or surgical prosthesis.

As shown in FIGS. 1, 5, and 8-11, tibial tray 14 includes anterior edge 40, posterior edge 42, medial edge 44, lateral edge 46, and boss 48. Boss 48 appears banana-shaped in the anterior plan view of FIG. 5 and projects proximally from support surface 41 (FIG. 1) of tibial tray 14. FIG. 1 further shows tibial tray 14 having a tibial stem 45 including stem fin 43 and stem shaft 47 distally extending from tibial tray 14. When tibial tray 14 is properly implanted in a tibia, tibial stem 45 projects into the tibia. Tibial tray 14 includes anterior rail 40A extending along anterior edge 40 between medial edge 44 and lateral edge 46. Anterior rail 40A increases in height from medial edge 44 to anterior edge 40 as well as from lateral edge 46 to anterior edge 40, which aids in fixation of bearing component 12 to tibial tray 14 as described below.

Tibial tray 14 also includes a support for bearing component 12. The support may be a tibial plateau or support surface 41 that is capable of supporting bearing component 12. The support may directly or indirectly communicate with bearing component 12. Where the communication is indirect, other components may be positioned between bearing component 12 and the support of tibial tray 14.

Figure 5:
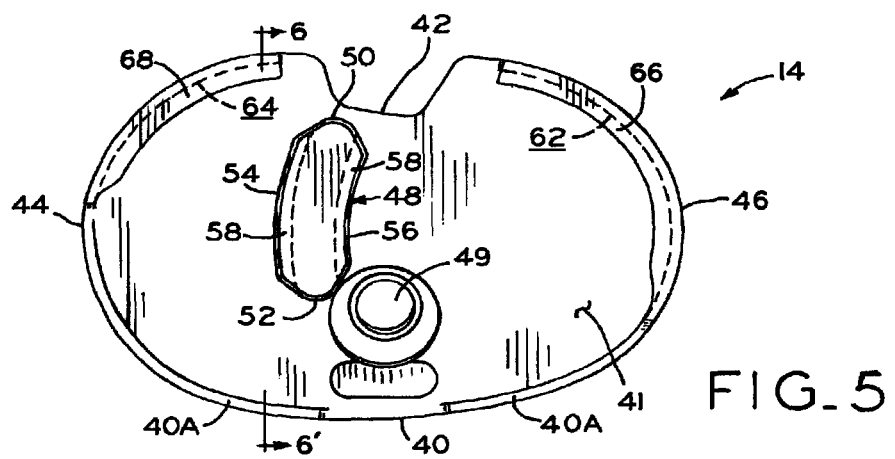
FIG. 5 is a proximal plan view of the tibial tray of the first embodiment.

As shown in FIG. 5, boss 48 includes posterior end 50 proximate to posterior edge 42 of tibial tray 14. Boss 48 further includes anterior end 52 opposite posterior end 50. Anterior end 52 is connected to posterior end 50 by a pair of elongated sides 54 and 56. Elongated side 56 faces lateral edge 46 of tibial tray 14 and forms a concave surface. Elongated side 54 faces medial edge 44 of tibial tray 14 and forms a convex surface. The curvature of elongated sides 54, 56 guides rotational movement of bearing component 12 atop tibial tray 14 to effect locking of bearing component 12 to tibial tray 14 as further described below.

Figure 6:
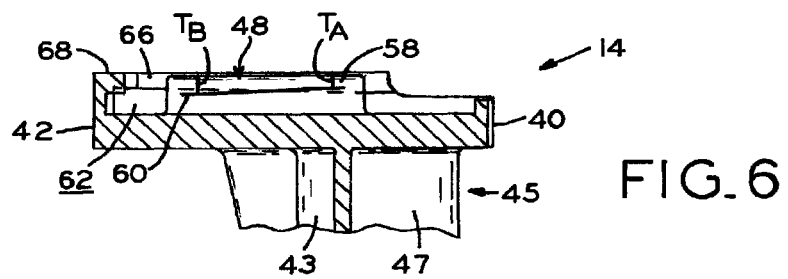
FIG. 6 is a cross-sectional view of the tibial tray of FIGS. 1 and 5 taken along lines 6-6' of FIGS. 1 and 5.

In one exemplary embodiment, boss 48 (FIG. 1) includes boss rail 58 projecting from edge 60 of each elongated side 54 and 46 of boss 48. Boss rail 58 has an increasing thickness in a first direction towards posterior end 50 of boss 48 shown by dimensions $T_A$ and $T_B$ where dimension $T_A$ is less than dimension $T_B$. Tibial tray 14 further has a pair of extended perimeter walls 62 and 64, each respectively positioned on the lateral edge 46 and the medial edge 44 of the tibial tray 14. Tibial tray 14 further includes a pair of projecting rails 66 and 68 that project inwardly from proximal edge 70 and 71 of each of extended perimeter walls 62 and 64, respectively. Projecting rail 68 has a thickness that increases in a first direction towards posterior edge 42 of tibial tray 14, as shown by thickness dimensions $T_{11}$ and $T_{22}$ for medially projecting rail 68, where $T_{11}$ has a lower thickness dimension measurement, or rather is less thick, than $T_{22}$. Projecting rail 66 has a thickness that increases in a second direction towards anterior edge 40 of tibial tray 14, as shown by thickness dimensions $T_1$ and $T_2$ for laterally projecting rail 66, where $T_2$ is less thick than $T_1$. FIG. 6, for example, illustrates lateral projecting rail 66 having an increasing thickness towards anterior edge 40.

Referring to FIGS. 1-4 and 7-12, bearing component 12 includes posterior edge 20, anterior edge 21, lateral edge 22, medial edge 24, and a pair of grooves 26 and 28 (FIGS. 2 and 12), each respectively positioned about lateral edge 22 and medial edge 24 of bearing component 12. As shown in FIGS. 1-3 and 12, groove 28 has a thickness increasing in a first direction towards posterior edge 20 of bearing component 12. The increasing thickness of groove 28 of bearing component 12 corresponds to the thickness of projecting rail 68 of tibial tray 14 (FIG. 1). Further, groove 26 has a thickness increasing in a second direction towards anterior edge 21 of bearing component 12. The increasing thickness of groove 28 of bearing component 12 corresponds to the thickness of projecting rail 66 of tibial tray 14. Lateral groove 26 has thickness dimensions $T_{33}$ and $T_{44}$ as illustrated in FIG. 1, and medial groove 28 has thickness dimensions $T_3$ and $T_4$. Referring to FIG. 3, thickness dimensions $T_{44}$ and $T_3$ are less thick than thickness dimensions $T_{33}$ and $T_4$, respectively. An end of groove 26 and 28 having an increased thickness is positionable to receive an end of projecting rail 66 and 68 that has a decreased thickness, i.e., is thinner. Grooves 26 and 28 may continue to receive projecting rails 66 and 68 until another end of projecting rails 66 and 68 having an increased thickness aligns with the end of grooves 26 and 28, also having a corresponding increased thickness, such that projecting rails 66 and 68 substantially fill grooves 26 and 28.

Figure 7:
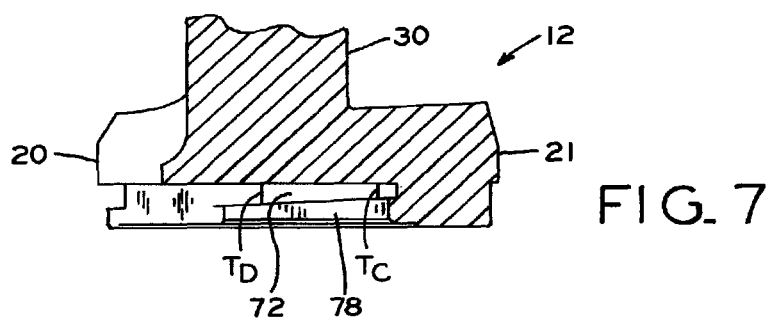
FIG. 7 is a cross-sectional view of the bearing component of FIG. 1 taken along line A-A of FIG. 1.
Figure 9:
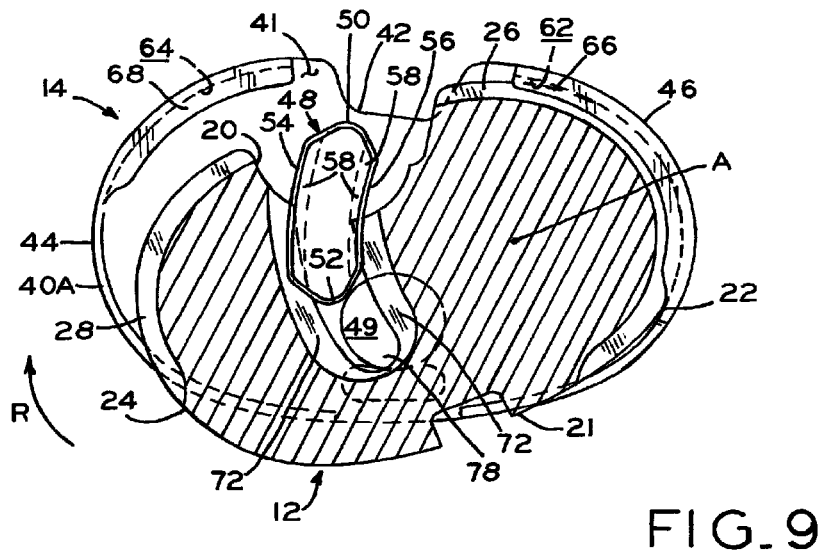
FIG. 9 is a proximal, partial sectional plan view of the tibial prosthesis showing the bearing component after rotation of the bearing component about a laterally displaced axis of rotation and into partial engagement with the tibial tray of the first embodiment.

Bearing component 12 further includes banana-shaped notch 78 shaped to receive boss 48 of tibial tray 14 (FIG. 2) and positioned in distal surface 80 of bearing component 12. As shown in FIGS. 1, 7 and 11, notch 78 has internal groove 72 that receives boss rail 58 of boss 48 of tibial tray 14 (FIG. 7). Internal groove 72 has a thickness that corresponds to the thickness of boss rail 58 of tibial tray 14 (FIG. 11). As shown in FIG. 7, internal groove 72 has thickness dimensions $T_C$ and $T_D$, where thickness dimension $T_C$ is less thick than thickness dimension $T_D$. Referring to FIG. 9, an end of internal groove 72 having an increased thickness receives an end of boss rail 58 having a decreased thickness as internal groove 72 is initially engaged with boss rail 58. Internal groove 72 is advanced further over boss rail 58 until the trailing end of boss rail 58, which has an increased thickness relative to the leading end, aligns with the end of internal groove 72 having a correspondingly increased thickness. When such alignment occurs, as shown in FIG. 11, boss rail 58 fills groove 72 to form a friction fit therebetween, thereby creating a fixed-bearing prosthesis.

While in one exemplary embodiment, the tibial tray may include a tray with a tibial stem, stem fin, and distally projecting stem shaft assembly that projects into the tibia on implantation, other types of tibial trays for use with this method are within the scope of this disclosure.

As described in more detail below, bearing component 12 is implanted along an anterior-medial insertion path I (FIG. 8) through incision S (FIG. 25) and onto tibial tray 14 to secure to the bearing component fixation structure (such as boss rail 58) of tibial tray 14, thereby avoiding the extensor mechanism of the knee during insertion. Bearing component 12 has at least one concave articulating surface to receive a corresponding articulating component, such as a femoral condyle or prosthesis. In the illustrative embodiments shown in the figures, bearing component 12 is fixedly secured to tibial tray 14 to form a fixed-bearing prosthesis.

The structure of tibial prosthesis 10 advantageously allows for an anterior-medial insertion of bearing component 12. Specifically, as mentioned above, the structure of tibial prosthesis 10 allows for implantation of bearing component 12 while avoiding the extensor mechanism of the knee. With tibial tray 14 implanted and securely fixed to a patient's tibia, bearing component 12 can be inserted through an incision made through the outer layers of skin and developed to provide access to the knee joint along an anterior-medial insertion trajectory.

Figure 8:
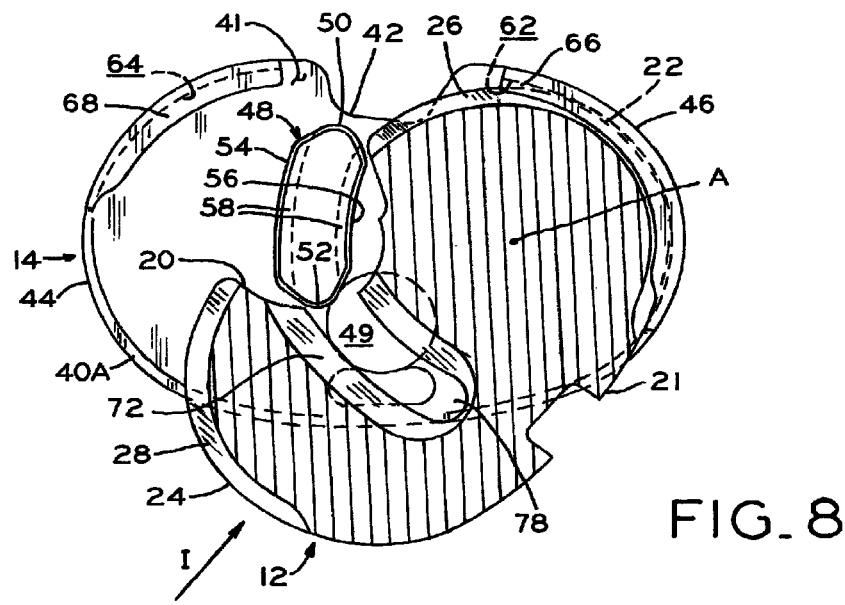
FIG. 8 is a proximal, partial sectional plan view of the tibial prosthesis showing the bearing component after an anterior-medial insertion of the same onto the tibial tray of the first embodiment.

Specifically, lateral edge 22 of bearing component 12 provides a leading edge for the insertion of bearing component 12 along an anterior-medial insertion trajectory. Stated another way, lateral edge 22 is the first aspect of bearing component 12 to reach the patient's knee during insertion. Thus, referring to a generally medial-lateral axis passing through the lateral-most and medial most points of bearing component 12 (where "medial" and "lateral" are with regard to the implanted orientation), insertion of bearing component 12 occurs with the medial-lateral axis of bearing component 12 generally aligned with the anterior-medial insertion direction. When the initial, anterior-medial insertion of bearing component 12 is complete, bearing component 12 is oriented relative to tibial tray 14 as shown in FIG. 8. Advantageously, this anterior-medial insertion trajectory presents the smallest possible aspect of bearing component 12 to incision S, and therefore allows incision S to be made as small as possible.

To achieve the position shown in FIG. 8, distal surface 80 (FIG. 4) of bearing component 12 is positioned atop anterior rail 40A of tibial tray 14. In this position, distal surface 80 of bearing component 12 is spaced a distance from support surface 41 defined by the height which anterior rail 40A projects anteriorly above support surface 41. As lateral edge 22 progresses along the anterior-medial insertion path and past anterior rail 40A, under surface 80 of bearing component 12 may, at its lateral edge, contact support surface 41 of tibial tray 14. Such contact is beneficial to facilitate insertion of projecting rail 66 of tibial tray into groove 26 of bearing component 12. This contact will also facilitate the later insertion of boss rail 58 into internal groove 72 of bearing component 12.

The generally linear anterior-medial insertion of bearing component 12 is complete when lateral edge 22 of bearing component 12 abuts lateral edge 46 of tibial tray 14. In this position, a portion of projecting rail 66 is received in groove 26. Further, as described above, distal surface 80 of bearing component 12 is not yet fully seated or flush with support surface 41 in the initial insertion position illustrated in FIG. 8.

To achieve final seating of bearing component 12 atop tibial tray 14, bearing component 12 is rotated along an axis generally parallel to a sagittal plane and positioned laterally of an anterior-posterior midline of tibial tray 14. An exemplary rotational direction R about axis A is illustrated in FIGS. 8 and 9. Referring to FIGS. 8 and 9, rotation of bearing component 12 along direction R positions boss rail 58 into internal groove 72 of bearing component 12.

In the initial phases of rotation R in which a leading end of boss rail 58 is first received into internal groove 72 of bearing component 12 (FIG. 8), a relatively thinner portion of boss rail 58 is adjacent to a relatively thicker opening portion of internal groove 72. A large clearance is therefore present between the thinner, leading edge of boss rail 58 and the adjacent, thickly-spaced walls of internal groove 72. Similarly, during the initial phases of rotation, a relatively thinner of portion of projecting rail 66 is received and positioned within a relatively thicker portion of groove 26 at the lateral aspect of the tibial prosthesis.

As rotation R continues as shown in FIG. 9, relatively thicker parts of boss rail 58 will occupy relatively thinner parts of internal groove 72, gradually converging such that the gap therebetween begins to close. At the end of rotation R as shown in FIG. 10, boss rail 58 reaches a final seated position to substantially fill internal groove 72. In an exemplary embodiment, the seated position of boss rail 58 and internal groove 72 defines an interference fit.

Similarly to rail 58 and groove 72, a relatively thinner portion of projecting rail 68 is first received within a relatively thicker portion of groove 28 at the medial aspect of the tibial prosthesis, and as rotation R continues, the relative thicknesses of projecting rail 68 and groove 28 will converge until the final seated position in which projecting rail 68 substantially fills groove 26.

In the rotation position illustrated in FIG. 9, distal surface 80 (FIG. 4) of bearing component 12 remains positioned atop anterior rail 40A of tibial tray 14. With projecting rails 66 and 68 moving toward a position in which rails 66, 68 fill grooves 26 and 28, respectively, the spacing of distal surface 80 of bearing component 12 from support surface 41 of tibial tray 14 will close the gap between the under surface of projecting rails 66 and 68 and the distal most surfaces defined by grooves 26 and 28, respectively. Similarly, the spacing caused by anterior boss 48 will close any gap between the under surface of boss rail 58 and the anterior most surface which forms internal groove 72 of bearing component 12. As rotation R continues, ever thicker portions of rails 66, 68, and 58 are encountered throughout grooves 26, 28, and 72, respectively.

In some instances, rotation R also causes elastic deformation of the walls forming grooves 26, 28, and 72. As rotation R progresses, such deformation increases pressure between various structures of bearing component 12 with tibial tray 14 (which structures interact as described above). The attendant increase in frictional forces between such structures increases resistance to further rotation R of bearing component 12 along rotational direction R until anterior edge 21 of bearing component 12 passes anterior rail 40A of tibial tray 14 and bearing component 12 snaps into position with a firm connection created by the cooperation of anterior edge 21 of bearing component 12 with an interior side of anterior rail 40A of tibial tray 14.

In a final seated position of bearing component 12 atop tibial tray 14, projecting rails 66 and 68 and boss rail 58 substantially fill grooves 26 and 28 and internal groove 72, respectively, and resist lift-off of bearing component 12 from tibial tray 14. Further, anterior edge 21 of bearing component 12 snaps into firm abutting engagement with the interior side of anterior rail 40A, which faces posterior edge 42 of tibial tray 14. This abutting engagement resists movement of bearing component 12 relative to tibial tray 14 along support surface 41 of tibial tray 14. The above-described interactions between structures on bearing component 12 and tibial tray 14 form locking mechanisms which cooperate to immobilize bearing component 12 with respect to tibial tray 14 in the final seated position, thereby forming a fixed-bearing prosthesis.

Optionally, an anterior rail of a tibial tray (e.g. anterior rail 40A of tray 14) may be absent as a locking mechanism. An alternative locking mechanism may be used to provide comparable securement, such as a distal tab projecting from a distal surface of a bearing component that is received into a proximal depression on a support surface of a tibial tray. An exemplary embodiment in accordance with this concept is shown within FIGS. 13-16 as the second embodiment of the present disclosure.

Except where specified otherwise, bearing component 112 is similar to bearing component 12 described above. Reference numbers in FIGS. 13-16 refer to analogous structures shown in FIGS. 1-12 and described above with respect to bearing component 12. For example, similar to bearing component 12, bearing component 112 is designed for anterior-medial insertion (along direction I, FIG. 14) through an incision (e.g., incision S, FIG. 25). Bearing component 112 is then positioned on top of tibial tray 114, and rotated to create a fit between bearing component 112 and tibial tray 114. While shown and described herein with specific reference to a left knee application, tibial prosthesis 110 may also be configured for use in a right knee application.

Figure 13:
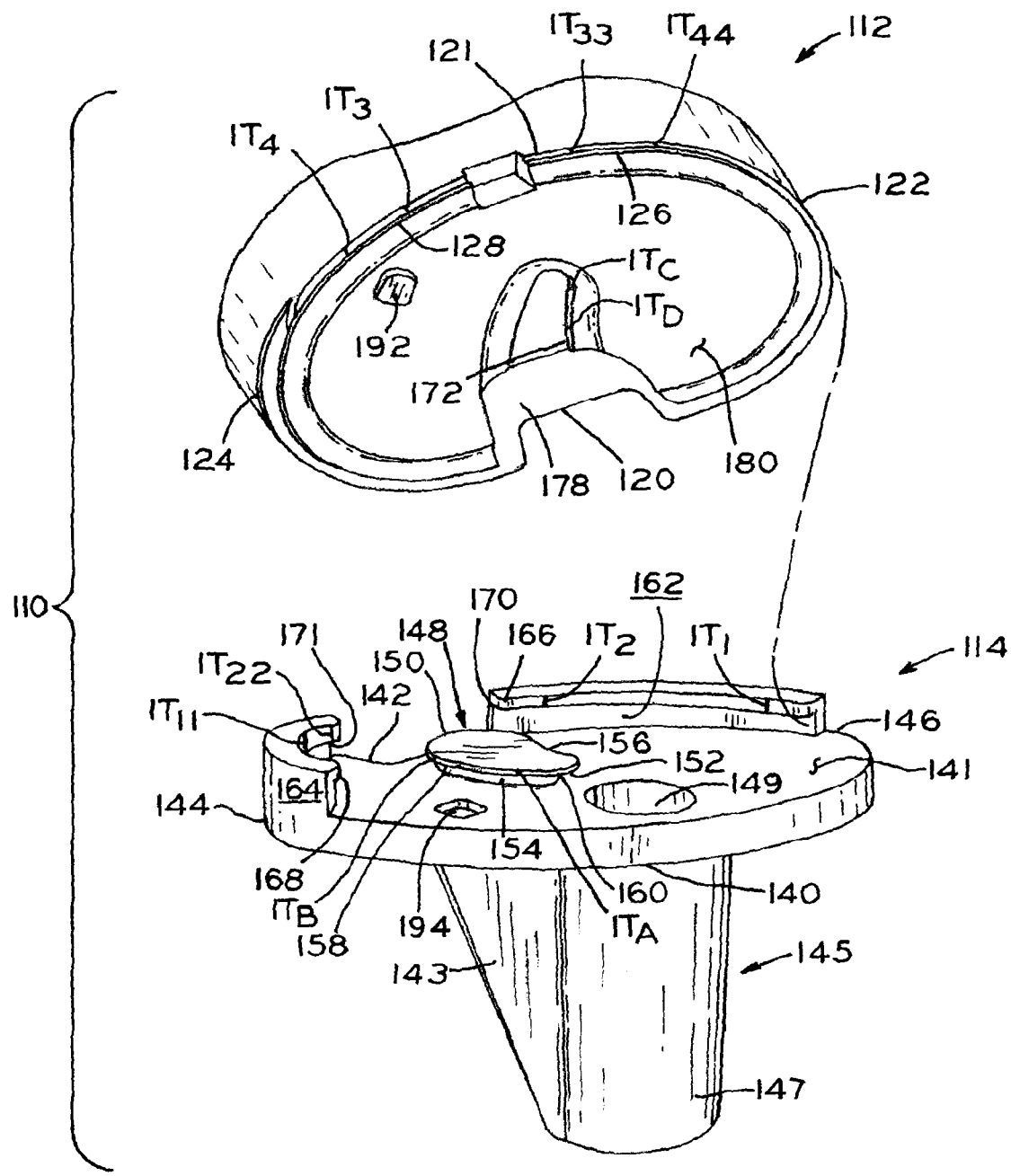
FIG. 13 is an exploded anterior perspective view of a tibial prosthesis made in accordance with a second embodiment of the present invention, including a bearing component and a tibial tray.

Referring to FIG. 13, tibial prosthesis 110 includes bearing component 112 and tibial tray 114, shown disassembled from one another. As illustrated in FIG. 14, bearing component 112 includes a pair of opposing articulating surfaces 116, 118 that are configured for articulation against opposing condyles of a femur or femoral prosthesis (not shown).

Bearing component 112 is securable to tibial tray 114. As shown in FIGS. 13-15, tibial tray 114 includes anterior edge 140, posterior edge 142, medial edge 144, lateral edge 146, and boss 148 projecting from support surface 141 of tibial tray 114 as shown in FIG. 13. FIG. 13 further shows tibial tray 114 having a tibial stem 145 including stem fin 143 and stem shaft 147 distally extending from bore 149 of tibial tray 114 and projecting into the tibia. Tibial tray 114 includes a support for bearing component 112. The support may be a support surface, such as support surface 141, which directly supports bearing component 112 in abutting contact. Alternatively, the support surface 141 may indirectly support bearing component 112, such as where other components are positioned between bearing component 112 and the support of tibial tray 114.

As shown in FIG. 15, boss 148 includes posterior end 150 proximate to posterior edge 142 of tibial tray 114. Boss 148 further includes anterior end 152 opposite posterior end 150 and connected to posterior end 150 by a pair of elongated sides 154 and 156. Elongated side 156 faces lateral edge 146 of tibial tray 114 and defines a generally concave surface. Elongated side 154 faces medial edge 144 of tibial tray 114 and defines a generally convex surface. The curvature of elongated sides 154, 156 guides rotational movement of bearing component 112 atop tibial tray 114 to effect locking of bearing component 112 to tibial tray 114 as further described below.

In the illustrated embodiment, boss 148 includes boss rail 158 projecting from edge 160 of each elongated side 154 and 146 of boss 148 (FIGS. 13 and 15). Boss rail 158 has an increasing thickness in a first direction towards posterior end 150 of boss 148, illustrated by dimensions $1T_A$ being less than dimension $1T_B$. Tibial tray 114 further has a pair of extended perimeter walls 162 and 164, each respectively positioned on the lateral edge 146 and the medial edge 144 of the tibial tray 114. Tibial tray 114 further includes a pair of projecting rails 166 and 168 that project inwardly from proximal edge 170 and 171 of each of extended perimeter walls 162 and 164, respectively. Projecting rail 168 has a thickness that increases in a first direction from medial edge 144 towards posterior edge 142 of tibial tray 114, as shown by thickness dimensions $1T_{11}$ of medially projecting rail 168, which is less than thickness dimension $1T_{22}$.

By contrast, projecting rail 166 has a thickness that increases in a second direction from posterior edge 142, around lateral edge 146 and towards anterior edge 140 of tibial tray 114, as shown by thickness dimensions $1T_1$ of laterally projecting rail 166 which is less than thickness dimension $1T_2$. For example, FIGS. 13 and 15 illustrate lateral projecting rail 166 having an increasing thickness towards anterior edge 140.

Referring to FIGS. 13, 14 and 16, bearing component 112 includes posterior edge 120, anterior edge 121, lateral edge 122, medial edge 124, and a pair of grooves 126 and 128, each respectively positioned on lateral edge 122 and medial edge 124 of bearing component 112 (FIG. 13). As shown in FIG. 13, medial groove 128 has a thickness increasing in a first direction from anterior edge 121 towards posterior edge 120 of bearing component 112. The increasing thickness of medial groove 128 corresponds to the increasing thickness of projecting rail 168 of tibial tray 114, as described above. Specifically, medial groove 128 has thickness dimensions $1T_3$ and $1T_4$ (FIG. 13), with thickness dimension $1T_3$ smaller than thickness dimension $1T_4$.

Similarly, lateral groove 126 has a thickness increasing in a second direction from posterior edge 120 towards anterior edge 121 of bearing component 112. The increasing thickness of lateral groove 126 corresponds to the increasing thickness of projecting rail 166 of tibial tray 114. Specifically, lateral groove 126 has thickness dimensions $1T_{33}$ and $1T_{44}$ as illustrated in FIG. 13, with thickness dimension $1T_{44}$ smaller than thickness dimension $1T_{33}$.

The ends of grooves 126, 128 having an increased thickness are sized to receive ends of projecting rails 166, 168 that have a decreased thickness with substantial clearance therebetween. Upon assembly, groove 126 and 128 are advanced over projecting rails 166 and 168, reducing the clearance therebetween until ultimately the thick ends of projecting rails 166 and 168 are respectively received within the correspondingly thick ends of groove 126 and 128, with no clearance therebetween. In an exemplary embodiment, rails 166, 168 define respective interference fits with grooves 126, 128.

Bearing component 112 further includes notch 178 shaped to receive boss 148 of tibial tray 114 (FIG. 13) and positioned in distal surface 180 of bearing component 112. As shown in FIG. 13, notch 178 has internal groove 172 that receives boss rail 158 of boss 148 of tibial tray 114 (FIG. 15). Internal groove 172 has a thickness that corresponds to the thickness of boss rail 158 of tibial tray 114 (FIG. 13). As shown in FIG. 13, internal groove 172 defines thickness dimension $1T_C$, which is less than thickness dimension $1T_D$. An end of internal groove 172 having an increased thickness initially receives the end of boss rail 158 having a decreased thickness such that a large clearance is defined therebetween, as shown in FIG. 14. Internal groove 172 is advanced over boss rail 158, reducing the clearance therebetween until ultimately the thick end of boss rail 158 is received within the correspondingly thick end of internal groove 172, with no clearance therebetween.

As shown in FIGS. 13 and 16, bearing component 112 includes distal tab 192 projecting distally from distal surface 180. Referring to FIGS. 13 and 15, tibial tray 114 includes proximal depression 194 positioned on support surface 141 for receipt of distal tab 192. A perimeter of proximal depression 194 is congruent to and slightly larger than a perimeter of distal tab 192. Distal tab 192 has a ramped geometry that slopes with respect to distal surface 180 from which distal tab 192 projects. For example, an anterior end of distal tab 192 facing anterior edge 121 of bearing component 112 is spaced further from distal surface 180 than a posterior end of distal tab 192 facing posterior edge 120 of bearing component 112. While such proximal depression and a distal tab are shown in the second and third embodiments of this disclosure, such proximal depression and distal tab elements optionally may be present or not present in any of the embodiments of this disclosure.

A method of inserting this embodiment is similar to the method described above for the first embodiment, but lacks the snap-fit locking mechanism provided by interaction between an anterior rail of the tibial tray and a corresponding anterior edge of a bearing component. Rather, the second embodiment of this disclosure uses a locking mechanism including distal tab 192 projecting from distal surface 180 of bearing component 112. When bearing component 112 is rotated to lock onto tibial tray 114, distal tab 192 is received into proximal depression 194 to prevent any further relative motion between bearing component 112 and tibial tray 114, thereby rendering prosthesis 110 a fixed-bearing prosthesis.

After the initial anterior-medial insertion of bearing component 112 (as described above with respect to bearing component 12), bearing component 112 undergoes rotation R about lateral axis A. During rotation R, the posterior end of distal tab 192, which extends a small distance from distal surface 180, comes into contact with support surface 141. Distal tab 192 is ramped from the posterior end to an anterior end such that the anterior end has the greatest distance, or height, from distal surface 180. As rotation R continues, support surface 141 rides along the ramp of distal tab 192 such that distal surface 180 of bearing component 112 is elevated from support surface 141 of tibial tray 114. As rotation continues about lateral axis A, distal tab 192 eventually "snaps" into proximal depression 194 such that an anterior wall positioned at the anterior end of distal tab 192 abuts a wall of proximal depression 194. When so engaged, tab 192 and depression 194 cooperate to prevent anterior movement of bearing component 112. Posterior movement is prevented via the interaction of projecting rails 166 and 168 with grooves 126 and 128, respectively.

In a final seated position of bearing component 112 atop tibial tray 114, projecting rails 166 and 168 and boss rail 158 substantially fill grooves 126, 128 and 172, respectively. Further, distal tab 192 is received into proximal depression 194 and distal surface 180 of bearing component 112 abuts support surface 141 of tibial tray 114. The interaction of projecting rails 166, 168 and boss rail 158 with grooves 126, 128 and internal groove 172, respectively, prevent lift-off of bearing component 112 from tibial tray 114, as well as sliding motion therebetween. Bearing component 112 is thus locked to tibial tray 114 in a final seated position in the manner of a fixed-bearing prosthesis.

FIGS. 17-20 illustrate an exemplary third embodiment of the present disclosure. The third embodiment is similar to the second embodiment except for the absence of the boss and corresponding notch features of the tibial tray and bearing component, respectively. Except where specified otherwise, bearing component 212 is similar to bearing component 12 described above. Reference numbers in FIGS. 17-20 refer to analogous structures shown in FIGS. 1-12 and described above with respect to bearing component 12. For example, similar to bearing component 12, bearing component 212 is designed for anterior-medial insertion (along direction I, FIG. 18) through an incision (e.g., incision S, FIG. 25). Bearing component 212 is then positioned on top of tibial tray 214, and rotated to create a fit between bearing component 212 and tibial tray 214. While shown and described herein with specific reference to a left knee application, tibial prosthesis 210 may also be configured for use in a right knee application.

Figure 17:
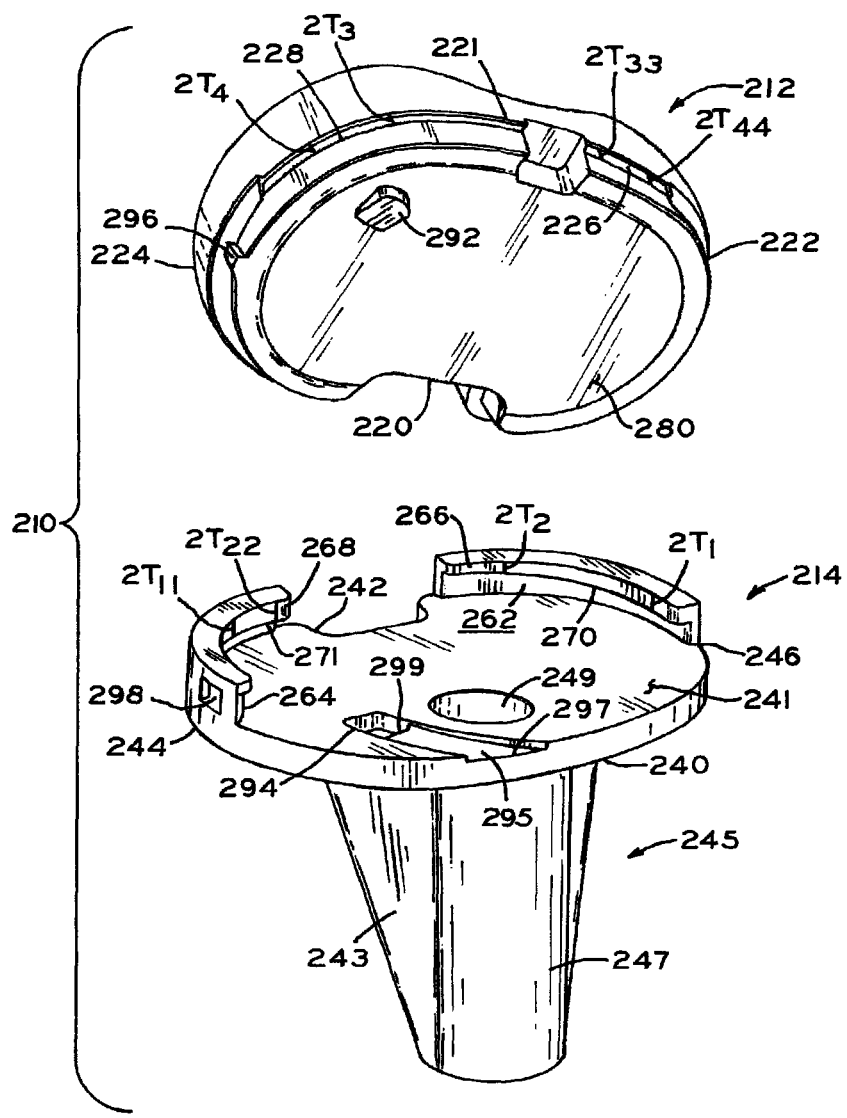
FIG. 17 is an exploded anterior perspective view of a tibial prosthesis made in accordance with a third embodiment of the present invention, including a bearing component and a tibial tray.
Figure 18:
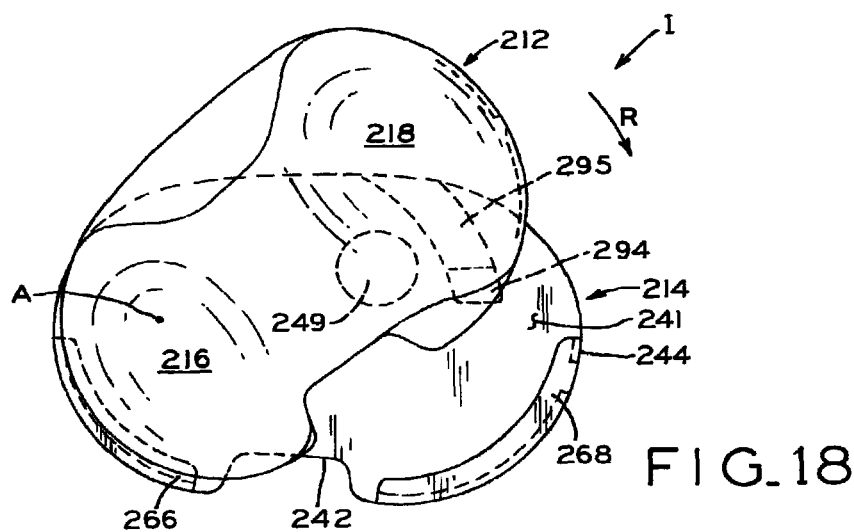
FIG. 18 a proximal plan view of the tibial prosthesis of the third embodiment including the tibial tray and a bearing component.

Referring to FIG. 17, tibial prosthesis 210 includes bearing component 212 and tibial tray 214, which are shown disassembled from one another. Referring to FIG. 18, bearing component 212 includes a pair of opposing articulating surfaces 216, 218 that are configured for articulation against opposing condyles of a femur or femoral prosthesis (not shown).

Figure 19:
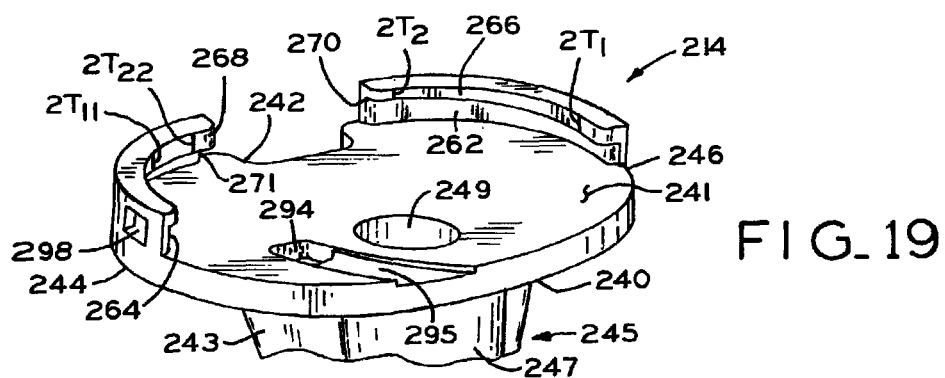
FIG. 19 is an anterior perspective view of the tibial tray of the third embodiment.

Bearing component 212 is securable to tibial tray 214. As shown in FIGS. 17-19, tibial tray 214 includes anterior edge 240, posterior edge 242, medial edge 244, lateral edge 246, and support surface 241. FIG. 17 further shows tibial tray 214 having a tibial stem 245 including stem fin 243 and stem shaft 247 distally extending from bore 249 of tibial tray 214 and projecting into the tibia. Tibial tray 214 includes a support for bearing component 212. The support may be a support surface, such as support surface 241, which directly supports bearing component 212 in abutting contact. Alternatively, the support surface 241 may indirectly support bearing component 212, such as where other components are positioned between bearing component 212 and the support of tibial tray 214.

Tibial tray 214 further has a pair of extended perimeter walls 262 and 264, each respectively positioned on lateral edge 246 and medial edge 244 of tibial tray 214. Medial perimeter wall 264 includes a plurality of surfaces defining the periphery of medially positioned aperture 298. Tibial tray 214 further includes a pair of projecting rails 266 and 268 that project inwardly from proximal edge 270 and 271 of each of extended perimeter walls 262 and 264, respectively.

Projecting rail 268 has a thickness that increases in a first direction towards posterior edge 242 of tibial tray 214, as shown by thickness dimensions $2T_{11}$ and $2T_{22}$ for medially projecting rail 268. Thickness dimension $2T_{11}$ is less than thickness dimension $2T_{22}$. For example, FIGS. 17 and 19 illustrate medial projecting rail 268 having a thickness that increases from anterior edge 240 towards posterior edge 242.

Projecting rail 266 has a thickness that increases in a second direction towards anterior edge 240 of tibial tray 214, as shown by thickness dimensions $2T_1$ and $2T_2$ for laterally projecting rail 266. Thickness dimension $2T_2$ is less than thickness dimension $2T_1$. For example, FIGS. 17 and 19 illustrate lateral projecting rail 266 having a thickness that increases from posterior edge 242 towards anterior edge 240.

Figure 20:
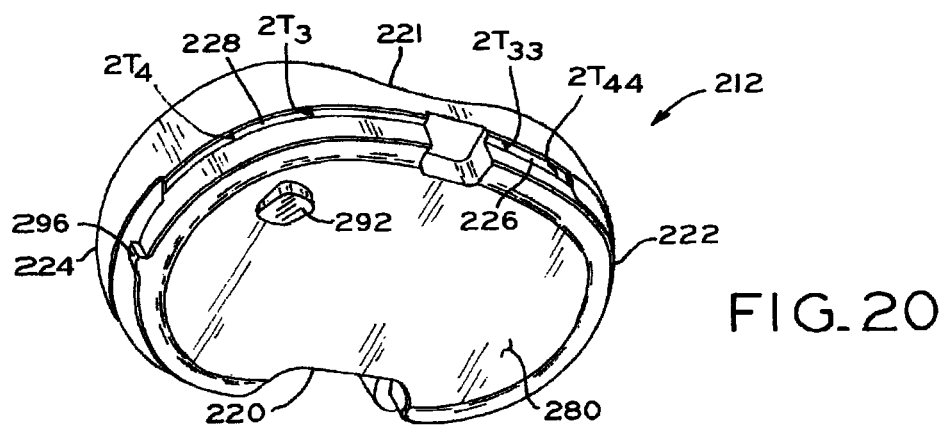
FIG. 20 is an anterior perspective view of the bearing component of the third embodiment.

Referring to FIGS. 17, 18, and 20, bearing components 212 includes posterior edge 220, anterior edge 221, lateral edge 222, medial edge 224, and a pair of grooves 226 and 228, each respectively positioned on lateral edge 222 and medial edge 224 of bearing component 212 (FIGS. 17 and 20). As shown in FIGS. 17 and 20, groove 228 has a thickness increasing in a first direction from anterior edge 221 towards posterior edge 220 of bearing component 212, such that the increasing thickness of groove 228 of bearing component 212 corresponds to the increasing thickness of projecting rail 268 of tibial tray 214. Specifically, medial groove 228 has thickness dimension $2T_3$, which is less than thickness dimension $2T_4$ as illustrated in FIG. 17.

Similarly, groove 226 has a thickness increasing in a second direction from posterior edge 220 towards anterior edge 221 of bearing component 212, such that the increasing thickness of groove 228 of bearing component 212 corresponds to the thickness of projecting rail 266 of tibial tray 214. Lateral groove 226 has thickness dimensions $2T_{44}$, which is less than thickness dimension $2T_{33}$ as illustrated in FIG. 17. The thick ends of grooves 226 and 228 initially receive the thin ends of projecting rails 266 and 268, thereby defining a large clearance therebetween. Upon assembly, grooves 226 and 228 are advanced over projecting rails 266 and 268, reducing the clearance therebetween until ultimately the thick ends of projecting rails 266 and 268 are respectively received within the correspondingly thick ends of groove 226 and 228, with no clearance therebetween.

As shown in FIGS. 17 and 20, bearing component 212 includes distal tab 292 projecting distally from distal surface 280 and medially positioned tab 296 projecting from medial edge 224 positioned for receipt into medially positioned aperture 298 of tibial tray 214. Similar to tibial tray 114 of FIGS. 13 and 15, tibial tray 214 includes proximal depression 294 positioned on support surface 241 for receipt of distal tab 292 where proximal depression 294 has a perimeter that is congruent to a perimeter of distal tab 292. Tibial tray 214 further includes ramped proximal groove 295 having anterior end 297 positioned at anterior edge 240 of tibial tray 214 and posterior end 299 adjacent proximal depression 294 (FIGS. 17 and 19). While ramped proximal groove 295 is shown in the third embodiment of this disclosure, it may also be included within the second embodiment of this disclosure. Alternatively, it may not be present in either the second or third embodiment of this disclosure.

A method of inserting this third embodiment is similar to the method described for the first embodiment above absent inclusion of an anterior rail and boss of the tibial tray to provide an additional locking mechanism. Rather, the third embodiment of this disclosure includes distal tab 292 projecting from distal surface 280 of bearing component 212 and a ramped proximal groove 295 that initially receives a posterior end of distal tab 292 during insertion of bearing component 212 onto tibial tray 214. Ramped proximal groove 295 includes a base and a pair of walls that are curved about the center of rotation R, such that groove 295 receives distal tab 292 in an arcuate manner when bearing component 212 is rotated along rotation R atop tibial tray 214. Ramped proximal groove is adjoined with proximal depression 294 that receives distal tab 292 upon a final seating of bearing component 212 onto tibial tray 214 in a similar manner as described above for the second embodiment.

This exemplary third embodiment further includes medially positioned tab 296 projecting from medial edge 224 of bearing component 212 that, like tab 292, defines a ramped surface. Medial tab 296 has a smallest height from medial edge 224 at a posterior end, and a largest height from medial edge 224 at an anterior end.

Bearing component 212 is rotated to lock onto tibial tray 214 in a manner similar to that described above for both the first and second embodiments with regard to the locking of the peripheral rails of varying thickness of the tibial tray with corresponding grooves in the bearing component. Particularly, bearing component 212 is rotated while the pair of projecting rails 266 and 268 of tibial tray 214 are progressively further received in the pair of grooves 226 and 228 of bearing component 212. However, in the third embodiment, distal tab 292 is received into ramped proximal groove 295 at the beginning of rotation R. As ramped proximal groove 295 has a base that is positioned lower, i.e., distal of support surface 241 of tibial tray 214, the gap formed between distal surface 280 and support surface 241 (which gap is created by the sloping of distal tab 292) is smaller as compared to the gap formed in the second embodiment.

As rotation R progresses, after distal tab 292 is initially received into ramped proximal groove 295, distal tab 292 is further urged along ramped proximal groove 295 into locking receipt with proximal depression 294 of tibial tray 214 (FIG.

20). Specifically, distal tab 292 slides along arcuate ramped proximal groove 295 until the perimeter of distal tab 292 is substantially congruent with the corresponding perimeter of proximal depression 294. When so received, distal tab 292 and proximal depression 294 cooperate to provide an additional locking mechanism which restricts rotation of the bearing component 212 relative to tibial tray 214.

After bearing component 212 locks to tibial tray 214, a wall at a posterior end of distal tab 292 cooperates with a wall of proximal depression 294 while the posterior wall of medially positioned tab 296 cooperates with a wall of medially positioned aperture 298 to prevent anterior movement of bearing component 212 along a plane including support surface 241. Movement in an opposite direction along the plane is prevented via the receipt of projecting rails 266 and 268 into grooves 226 and 228, respectively. The cooperation of projecting rails 266 and 268 into grooves 226 and 228 further assists with preventing lift-off of bearing component 212 from tibial tray 214.

Another locking mechanism of prosthesis 210 may be actuated during rotation R. The anterior end of medially positioned tab 296, which projects from medial edge 224 of bearing component 212, initially passes onto perimeter wall 264 during rotation R. Wall 264 continues to slide up the ramped surface of medially positioned tab 296 until medially positioned tab 296 is snaps into engagement with medially positioned aperture 298 of tibial tray 214. After such engagement, the posterior wall of medially positioned tab 296 (i.e., the wall of tab 296 with the largest height differential) abuts an adjacent wall of medially positioned aperture 298 to prevent sliding or rotating movement of bearing component 212 along a plane including support surface 241, thereby contributing to the "fixed-bearing" configuration of prosthesis 210.

In yet another exemplary embodiment, a tibial tray may have a tibial boss defining an angled geometry, relative to a sagittal plane, which allows a bearing component to lockingly connected to the tibial tray along a single anterior-medial insertion trajectory (i.e., without separate rotation as described above).

As shown in a fourth embodiment illustrated in FIGS. 21-24, bearing component 312 may be inserted along a path defining a medially oriented angle (a) from an anteroposterior reference axis 381. In the illustrated embodiment, axis 381 passes through an anterior edge of tibial tray 314 (FIG. 22) and is parallel to a sagittal plane. Except where specified otherwise, bearing component 312 is similar to bearing component 12 described above. Reference numbers in FIGS. 21-24 refer to analogous structures shown in FIGS. 1-12 and described above with respect to bearing component 12. While shown and described herein with specific reference to a left knee application, tibial prosthesis 310 may also be configured for use in a right knee application.

Figure 21:
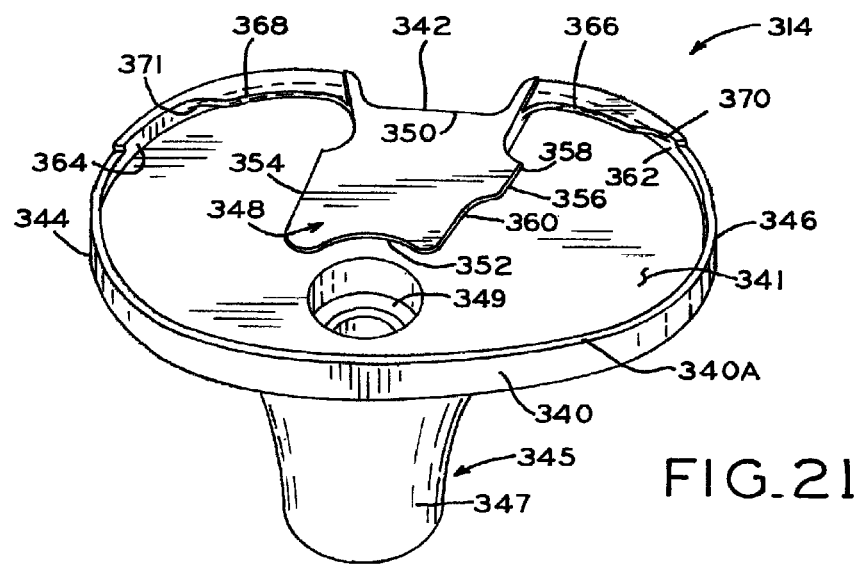
FIG. 21 is a proximal perspective view of the tibial tray of a tibial prosthesis made in accordance with a fourth embodiment of the present invention.
Figure 22:
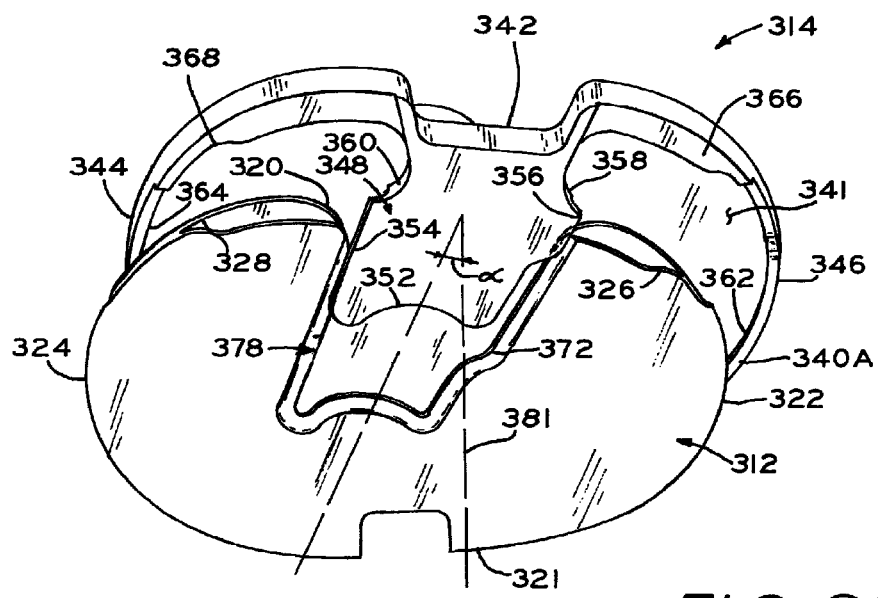
FIG. 22 is a proximal plan view of the tibial prosthesis of the fourth embodiment including the tibial tray and a bearing component.

FIG. 21 further shows tibial tray 314 having a tibial stem 345 including stem shaft 347 distally extending from bore 349 of tibial tray 314 and projecting into the tibia. As illustrated in FIG. 22, bearing component 312 may be inserted at an angle ranging from about 8 degrees to about 10 degrees from axis 381. Alternatively, bearing component 312 may be inserted at an angle ranging from as little as about zero or 1 degree, and as much as about 30 degrees or 90 degrees, with respect to axis 318. It is contemplated that such angle of insertion may be within any range defined by any of the foregoing values.

Once Bearing component 312 may then be pressed into tibial tray 314 to lock bearing component 312 to tibial tray 314 (FIG. 24), with, e.g., a snap fit or an interference fit. Rail 366 and 368 of a substantially constant thickness may be inserted into groove 326 and 328, respectively, having a corresponding substantially constant thickness, until a fit is achieved in which rails 366 and 368 fully received within grooves 326 and 328, respectively. Additional securement may be provided by boss 348 on tibial tray 314, which cooperates with a correspondingly shaped notch 378 on bearing component 312. Notch 378 receives boss 348 of the tibial tray 314 (FIG. 22) for locking engagement therebetween.

Advantageously, boss 348 may be canted to accommodate the insertion angles disclosed herein, which allows tibial bearing component 312 to avoid the extensor mechanism of the knee (FIG. 25) as bearing component 312 is secured to tibial tray 314. A boss of any shape and a correspondingly shaped notch that receives the boss are within the scope of this disclosure. Exemplary shapes and configurations for boss 348 are disclosed in U.S. patent application Ser. No. 13/189,328, entitled TIBIAL PROSTHESIS, filed on Jul. 22, 2011, and assigned to the present assignee, the entire disclosure of which is hereby expressly incorporated by reference herein.

Tibial prosthesis 310 includes bearing component 312 having at least one concave articulating surface configured for articulation against opposing condyles of a femur or femoral prosthesis (not shown). As shown in FIG. 21, tibial tray 314 has anterior edge 340, anterior rail 340A, posterior edge 342, lateral edge 346, medial edge 344, and includes a support for bearing component 312. The support may be a support surface, such as support surface 341, which directly supports bearing component 312 in abutting contact. Alternatively, the support surface 341 may indirectly support bearing component 312, such as where other components are positioned between bearing component 312 and the support of tibial tray 314.

Tibial tray 314 also includes boss 348 that has posterior end 350, anterior end 352, and a pair of elongated sides 354 and 356, each facing one of the medial and lateral edges 344 and 346, respectively, of tibial tray 314. Elongated sides 354 and 356 define laterally and medially angled surfaces which combine to define a central axis. The central axis is angularly offset from anteroposterior reference axis 381, which is positioned through anterior edge 321 of tibial tray 314 and parallel to the sagittal plane as noted above. This angular offset defines an offset axis angle $\alpha$ which ranges from about 8 to about 10 degrees with respect to axis 381.

However, it is contemplated that offset axis angle $\alpha$ may range from about 0 degrees to about 90 degrees, and may an angle as small as 0, 1, 2, 3, 4, 5, 6, 7, or 8 degrees, or as great as 9, 10, 20, 30, 40, 50, 60, 70, 80, or 90 degrees, or may be any angle within any range defined by the foregoing angle values.

The angled surface of lateral elongated side 356 faces lateral edge 346 of tibial tray 314, and the angled surface of medial elongated side 354 faces medial edge 344 of tibial tray 314. The angled surface of lateral elongated side 356 has a lateral side angle that is angled relative to offset axis $\alpha$, and the angled surface of medial elongated side 354 has a medial side angle that is angled relative to offset axis $\alpha$. In an exemplary embodiment, the lateral side angle and the medial side angle may each range from about 0 degrees to about 15 degrees, or from about 5 degrees to 10 degrees. It is further contemplated that the medial and lateral side angles may be an angle as small as 0, 1, 2, 3, 4, 5, 6, or 7 degrees or as great as 8, 9, 10, 11, 12, 13, 14, or 15 degrees, or may be any angle within any range defined by the foregoing angle values.

Boss 348 has boss rail 358 that transversely projects from an edge 360 of each of elongated sides 354 and 356 and has a substantially constant thickness (FIG. 21). Tibial tray 314 further includes a pair of extended perimeter walls 362 and 364. Extended perimeter wall 362 is positioned on lateral edge 346 of tibial tray 314. Extended perimeter wall 364 is positioned on medial edge 344 of tibial tray 314. Tibial tray 314 also includes a pair of projecting rails 366 and 368 that project inwardly from each of extended perimeter walls 362 and 364, respectively. Each projecting rail 366 and 368 has a substantially constant thickness. Alternatively, each projecting rail 366 and 368 may have an increasing thickness in a direction from anterior edge 340 towards posterior edge 342 of tibial tray 314.

As illustrated in FIGS. 22 and 23, bearing component 312 includes posterior edge 320, anterior edge 321, lateral edge 322, medial edge 324, and a pair of grooves 326 and 328. Lateral groove 326 is positioned on lateral edge 322 of bearing component 312, and medial groove 328 is positioned on medial edge 324 of bearing component 312. Each groove 326 and 328 has a thickness corresponding to a thickness of projecting rails 366 and 368, respectively. Alternatively, each groove 326 and 328 may have an increasing thickness in a direction from anterior edge 321 towards posterior edge 320 of bearing component 312, such that the increasing thickness corresponds to the correspondingly increasing thickness of projecting rails 366 and 368, respectively.

Notch 378 in bearing component 312 is shaped to receive boss 348 of tibial tray 314 and includes internal groove 372 for receipt of boss rail 358, which is shown in a final seated position in FIG. 24. In an exemplary embodiment, boss rail 358 and internal groove 372 define an interference fit therebetween such that some deformation of groove 372 and/or boss rail 358 occurs upon mating. Internal groove 372 has a substantially constant thickness that corresponds to the thickness of boss rail 358. Alternatively, boss rail 358 and, similarly, internal groove 372 may have an increasing thickness in a first direction from anterior edge 340 towards posterior edge 342 of tibial tray 314.

After tibial tray 314 is positioned within a knee through an incision made to provide access to the knee during surgery, bearing component 312 is inserted atop tibial tray 314 in a manner that avoids the extensor mechanism of the knee (FIG. 25), as discussed above. Particularly, bearing component 312 is inserted through incision S (FIG. 25) in an anterior-medial insertion direction to an initial reception position where a posterior end of notch 378 on bearing component 312 receives the leading, anterior end 352 of boss 348. Internal groove 372 is advanced over boss rail 358 as bearing component 312 is inserted onto tibial tray 314 along angle α ranging, for example, from about 0 to about 90 degrees from a sagittal plane as described above.

When internal groove 372 "bottoms out" against boss rail 358, such that no further anterior-medial movement of bearing component 312 relative to tibial tray 314 is possible, bearing component 312 is in a final, fully-installed position. In this final position, projecting rails 366 and 368 are received by and substantially fill grooves 326 and 328, respectively.

During the anterior-medial insertion process (described above), bearing component 312 is urged atop tibial tray 314 as projecting rails 366 and 368 substantially fill grooves 326 and 328. At the same time, internal groove 372 is advanced over boss rail 358 until any gaps between surfaces of the rails 366, 368, and 358, and surface creating grooves 326, 328, and 372, respectively are filled.

In order to secure bearing component 312 in the fully installed position on tibial tray 314, anterior rail 340A is provided on tibial tray 314 to engage in a final snap-fit connection with bearing component 312. During the advancement of grooves 326 and 328 and internal groove 372 receive respective rails 366, 368, and boss rail 358, walls forming grooves 326 and 328 and internal groove 372 may experience elastic deformation as anterior rail 340A urges the distal surface of bearing component 312 upwardly. Such deformation, coupled with frictional forces experienced by the interaction of these portions of bearing component 312 and tibial tray 314, increases resistance to movement of bearing component 312 along angle α.

When anterior edge 321 of bearing component 312 passes anterior rail 340A of tibial tray 314, bearing component 312 snaps into position in a firm connection created by the operation of anterior edge 321 with an interior side of anterior rail 340A. In a final seated position of bearing component 312 atop tibial tray 314, projecting rails 366 and 368 and boss rail 358 substantially fill grooves 326 and 328 and internal groove 372, respectively, and resist lift-off and translation of bearing component 312 relative to tibial tray 314. The cooperation of the above-described locking mechanisms lock bearing component 312 to tibial tray 314 in the final seated position, such that prosthesis 310 is a fixed-bearing prosthesis.

The above-described exemplary embodiments are generally directed to a "primary" prosthesis, i.e., a prosthesis which is designed to be implanted in a natural knee which retained natural articular surfaces prior to the implantation. However, it is also contemplated that prosthetic knee components made in accordance with the present disclosure may also be used in a revision procedure, in which one or more previously-implanted knee prosthesis components are removed and replaced. For example, the exemplary tibial trays described above are amenable to reuse in a revision procedure, such that the tibial tray is left in its originally-implanted position on the tibia and only the tibial bearing component is replaced. Advantageously, leaving the tibial tray in place allows the tibial bearing component to be replaced without further resection of the tibia, which might otherwise be required where the tibial tray is removed.

Additional features of tibial trays and tibial bearing components, which may be combined with prostheses in accordance with the present disclosure, are disclosed in U.S. Provisional Patent Application Ser. No. 61/381,800, filed on Sep. 10, 2010 and entitled TIBIAL PROSTHESIS FACILITATING ROTATIONAL ALIGNMENT, and in U.S. patent application Ser. Nos. 13/189,336, 13/189,338, and 13/189,339, each entitled ASYMMETRIC TIBIAL COMPONENTS FOR A KNEE PROSTHESIS and filed on Jul. 22, 2011, the entire disclosures of which are hereby expressly incorporated herein by reference.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of inserting a bearing component onto a tibial tray implanted on a knee, the method comprising:

positioning the tibial tray within the knee via an incision, the tibial tray having a support surface sized to receive the bearing component and a boss projecting proximally from the support surface;

inserting the bearing component, while avoiding an extensor mechanism of the knee, through the incision in an anterior-medial insertion direction to position a distal surface of the bearing component atop the support surface of the tibial tray, the bearing component having a notch formed in the distal surface and configured to receive the boss of the tibial tray;

rotating the bearing component about an axis of rotation positioned laterally of an anterior-posterior midline of the tibial tray to move the bearing component to a final seated position on the tibial tray, wherein the boss of the tibial tray includes a rail, the notch of the bearing component includes a groove, and the step of rotating the bearing component about an axis of rotation includes a portion of the rail being received in the groove formed in the notch;

wherein subsequent rotation of the bearing component results in an interference fit between the rail of the boss and the groove of the notch.

2. The method of claim 1, wherein the rail is disposed at a posterior end of the tibial tray, the groove is disposed at a posterior end of the bearing component, and the final seated position of the bearing component includes engagement between the groove and the rail to secure the bearing component to the tibial tray.

3. The method of claim 2, wherein the rail includes a medial projecting rail and a lateral projecting rail, and the groove includes a medial groove for engagement with the medial projecting rail and a lateral groove for engagement with the lateral projecting rail.

4. A method of inserting a bearing component onto a tibial tray via an incision providing access to a knee, the knee having an extensor mechanism, the method comprising:

providing the tibial tray having a support surface sized to receive the bearing component;

positioning the tibial tray within the knee via the incision;

providing the bearing component having at least one concave articulating surface and an opposing distal surface;

inserting the bearing component, while avoiding the extensor mechanism, through the incision in an anterior-medial insertion direction to position the distal surface of the bearing component atop the support surface of the tibial tray;

seating the bearing component onto the tibial tray comprising rotating the bearing component about an axis of rotation displaced laterally of an anterior-posterior midline of tibial tray; and mating a boss and notch of the bearing component and the tibial tray, the boss and notch having corresponding shapes that are configured to allow for the rotating of the bearing component to provide a final alignment of the bearing component with the tibial tray, the boss and notch are configured to provide for a locking engagement of the bearing component with the tibial tray in the manner of a fixed-bearing prosthesis.

5. The method of claim 4, wherein:

the step of providing the bearing component comprises providing the bearing component including a distal tab projecting distally from the distal surface, the step of providing the tibial tray comprises providing the tibial tray including a proximal depression in the support surface, the proximal depression sized for receipt of the distal tab of the bearing component, the proximal depression having a proximal depression perimeter, the distal tab having a distal tab perimeter, the proximal depression perimeter congruent to the distal tab perimeter, and the step of seating the bearing component onto the tibial tray further comprises positioning the distal tab of the bearing component into the proximal depression of the tibial tray.

6. The method of claim 5, wherein the step of providing the tibial tray comprises providing the tibial tray including a ramped proximal groove in the support surface for receipt of the distal tab of the bearing component, and wherein the step of seating the bearing component onto the tibial tray further comprises urging the distal tab of the bearing component into the ramped proximal groove of the tibial tray such that the distal tab is received in the ramped proximal groove prior to being received into the proximal depression.

7. The method of claim 4, wherein the step of providing the tibial tray comprises providing the tibial tray including a medial perimeter wall having a plurality of surfaces defining a medially positioned aperture, wherein the step of providing the bearing component comprises providing the bearing component including a medial edge having medially positioned tab projecting from the medial edge, the medially positioned tab shaped for receipt into the medially positioned aperture of the tibial tray, and wherein the step of seating the bearing component onto the tibial tray further comprises positioning the medially positioned tab of the bearing component into the medially positioned aperture of the tibial tray.

8. The method of claim 4, wherein the step of inserting the bearing component comprises inserting the bearing component along an angle ranging from greater than zero to 90 degrees from a sagittal plane.

9. The method of claim 4, wherein the step of inserting the bearing component comprises inserting the bearing component along an angle ranging from greater than zero to 30 degrees from a sagittal plane.

10. The method of claim 4, wherein the step of inserting the bearing component comprises inserting the bearing component along an angle ranging from 8 to 10 degrees from a sagittal plane.

11. The method of claim 4, wherein the step of providing the tibial tray comprises providing the tibial tray including the boss and a boss rail, the boss rail having an increasing thickness in a direction from an anterior end of the tibial tray towards a posterior end of the tibial tray, and wherein the step of providing the bearing component comprises providing the bearing component comprising the notch shaped to receive the boss, the notch comprising an internal groove sized to receive of the boss rail, the internal groove having an increasing thickness corresponding to the increasing thickness of the boss rail.

12. The method of claim 11, wherein the step of seating the bearing component onto the tibial tray comprises:

advancing the boss of the tibial tray into the notch of the bearing component, and rotating the bearing component until the boss rail of the tibial tray forms the locking engagement with the internal groove of the notch of the bearing component.

13. The method of claim 4, wherein the step of positioning the tibial tray comprises positioning the tibial tray including the boss including:

a concave lateral side facing a lateral edge of the tibial tray, and a convex medial side facing a medial edge of the tibial tray; and wherein the step of seating the bearing component onto the tibial tray comprises:

advancing the boss of the tibial tray into the notch, and rotating the bearing component until medial and lateral projecting rails of the tibial tray form a locking engagement with medial and lateral grooves of the bearing component, respectively.

14. A method of inserting a bearing component onto a tibial tray via an incision providing access to a knee, the knee having an extensor mechanism, the method comprising:

providing the tibial tray having a support surface sized to receive the bearing component;

positioning the tibial tray within the knee via the incision, wherein the step of positioning the tibial tray comprises positioning the tibial tray including a boss including:

a concave lateral side facing a lateral edge of the tibial tray, a convex medial side facing a medial edge of the tibial tray, and a boss rail projecting transversely from each of the concave lateral side and the convex medial side, the boss rail having an increasing thickness in a first direction from an anterior end of the boss towards a posterior end of the boss;

providing the bearing component having at least one concave articulating surface and an opposing distal surface, wherein the bearing component comprises a notch shaped to receive the boss of the tibial tray;

inserting the bearing component, while avoiding the extensor mechanism, through the incision in an anterior-medial insertion direction to position the distal surface of the bearing component atop the support surface of the tibial tray; and seating the bearing component onto the tibial tray, wherein the step of seating the bearing component onto the tibial tray comprises:

advancing the boss of the tibial tray into the notch, and rotating the bearing component until the medial and lateral projecting rails of the tibial tray form a locking engagement with the medial and lateral grooves of the bearing component, respectively.

15. The method of claim 14, wherein the step of providing the tibial tray comprises providing the tibial tray including:

a lateral perimeter wall positioned at the lateral edge of the tibial tray;

a medial perimeter wall positioned at the medial edge of the tibial tray;

a medial projecting rail projecting from the medial perimeter wall towards the lateral edge of the tibial tray, the medial projecting rail having an increasing thickness in a first direction from an anterior edge of the tibial tray towards a posterior edge of the tibial tray, and a lateral projecting rail projecting from the lateral perimeter wall towards the medial edge of the tibial tray, the lateral projecting rail having an increasing thickness in a second direction from the posterior edge of the tibial tray towards the anterior edge of the tibial tray; and wherein the step of positioning the bearing component onto the tibial tray in an anterior-medial direction comprises providing the bearing component including:

a posterior edge;

an anterior edge;

a medial edge having a medial groove formed therein, the medial groove having an increasing thickness in a third direction from the anterior edge towards the posterior edge of the bearing component, the increasing thickness of the medial groove corresponding to the increasing thickness of the medial projecting rail, such that the medial projecting rail defines an interference fit with the medial groove; and a lateral edge having a lateral groove formed therein, the lateral groove having an increasing thickness in a fourth direction from the posterior edge towards the anterior edge of the bearing component, the increasing thickness of the lateral groove corresponding to the increasing thickness of the lateral projecting rail, such that the lateral projecting rail defines an interference fit with the lateral groove.

\* \* \* \* \*